(12) United States Patent
Wu

(10) Patent No.: US 10,561,303 B2
(45) Date of Patent: Feb. 18, 2020

(54) OPTICAL PROBES WITH CORRECTION COMPONENTS FOR ASTIGMATISM CORRECTION

(71) Applicant: Canon U.S.A., Inc., Melville, NY (US)

(72) Inventor: Tzu-Yu Wu, Malden, MA (US)

(73) Assignee: Canon U.S.A., Inc., Melville, NY (US)

( * ) Notice: Subject to any disclaimer, the term of this patent is extended or adjusted under 35 U.S.C. 154(b) by 26 days.

(21) Appl. No.: 15/879,269

(22) Filed: Jan. 24, 2018

(65) Prior Publication Data
US 2019/0223699 A1    Jul. 25, 2019

(51) Int. Cl.
| | | |
|---|---|---|
| *F21V 7/04* | (2006.01) | |
| *A61B 1/00* | (2006.01) | |
| *A61B 5/00* | (2006.01) | |
| *A61B 1/07* | (2006.01) | |
| *G02B 23/24* | (2006.01) | |

(52) U.S. Cl.
CPC ...... *A61B 1/00188* (2013.01); *A61B 1/00096* (2013.01); *A61B 1/00177* (2013.01); *A61B 1/07* (2013.01); *A61B 5/0035* (2013.01); *A61B 5/0066* (2013.01); *A61B 5/0071* (2013.01); *A61B 5/0084* (2013.01); *G02B 23/243* (2013.01); *G02B 23/2423* (2013.01)

(58) Field of Classification Search
CPC ... A61B 1/00188; A61B 1/07; A61B 1/00096; A61B 5/0071; A61B 5/0035; A61B 5/0066; A61B 5/0084
USPC ........................................................ 362/555
See application file for complete search history.

(56) References Cited

U.S. PATENT DOCUMENTS

| | | | |
|---|---|---|---|
| 5,554,100 A | * | 9/1996 | Leiner ................ A61B 1/00179 385/117 |
| 6,433,937 B1 | | 8/2002 | Konno |
| 6,445,939 B1 | | 9/2002 | Swanson |
| 6,501,878 B2 | | 12/2002 | Hughes |
| 6,564,087 B1 | | 5/2003 | Pitris et al. |

(Continued)

FOREIGN PATENT DOCUMENTS

| | | |
|---|---|---|
| JP | H04-60608 A | 2/1992 |
| WO | 2015116939 A1 | 8/2015 |
| WO | 2016077252 A1 | 5/2016 |

OTHER PUBLICATIONS

Max Born, et al., Principles of Optics: Electromagnetic Theory of Propagation, Interference and Diffraction of Light, 6th ed., Pergamon Press, 1980, pp. 169-174 and 214-217 (and title and copyright pages included) (The year of publication for this reference is sufficiently earlier than the effective U.S. filing date and any foreign priority date so that the particular month of publication is not in issue.).

(Continued)

*Primary Examiner* — Ali Alavi
(74) *Attorney, Agent, or Firm* — Canon U.S.A., Inc. IP Division

(57) ABSTRACT

An optical probe comprises a light-guiding component, an optical component, a light-reflecting component that is configured to receive light from the optical component and direct the light along a path, and a correction component. The correction component lies in the path, the correction component has an optical power, and the correction component has a center of curvature that substantially coincides with an optical axis of the optical component.

28 Claims, 24 Drawing Sheets

(56) References Cited

U.S. PATENT DOCUMENTS

| | | | |
|---|---|---|---|
| 6,801,375 B2 | 10/2004 | Hayashide | |
| 6,954,296 B2 | 10/2005 | Takakubo | |
| 7,366,376 B2 | 4/2008 | Shishkov | |
| 7,457,044 B2 | 11/2008 | Ohzawa | |
| 7,492,987 B2 | 2/2009 | Yeik et al. | |
| 7,680,378 B2 | 3/2010 | Alphonse | |
| 7,813,609 B2 | 10/2010 | Petersen | |
| 8,180,134 B2 | 5/2012 | Wang | |
| RE43,875 E | 12/2012 | Shishkov | |
| 8,425,500 B2* | 4/2013 | Hanley | A61B 18/24 606/15 |
| 8,515,221 B2 | 8/2013 | Flanders | |
| 8,582,934 B2 | 11/2013 | Adler | |
| 8,781,287 B2 | 7/2014 | Flanders | |
| 8,971,679 B2 | 3/2015 | Ho | |
| RE45,512 E | 5/2015 | Tearney | |
| 9,036,966 B2 | 5/2015 | Bhagavatula | |
| 9,069,122 B2 | 6/2015 | Takeuchi | |
| 9,087,368 B2 | 7/2015 | Tearney | |
| 9,164,272 B2 | 10/2015 | Maillard | |
| 9,318,810 B2 | 4/2016 | Zelenski | |
| 9,488,782 B2 | 11/2016 | Griffin | |
| 9,662,173 B1 | 5/2017 | Griffin | |
| 10,234,676 B1 | 3/2019 | Elmaanaoui | |
| 2002/0076180 A1* | 6/2002 | Miyano | G02B 6/06 385/117 |
| 2004/0133071 A1* | 7/2004 | Alekseenko | A61B 1/00096 600/101 |
| 2005/0165315 A1 | 7/2005 | Zuluaga | |
| 2006/0067620 A1 | 3/2006 | Shishkov | |
| 2007/0159601 A1 | 7/2007 | Ho et al. | |
| 2007/0233396 A1 | 10/2007 | Tearney | |
| 2008/0013960 A1 | 1/2008 | Tearney | |
| 2009/0244545 A1 | 10/2009 | Toida | |
| 2009/0262361 A1 | 10/2009 | Tanioka et al. | |
| 2009/0306477 A1 | 12/2009 | Togino | |
| 2011/0137124 A1 | 6/2011 | Milner | |
| 2011/0141759 A1 | 6/2011 | Smith | |
| 2012/0101374 A1 | 4/2012 | Tearney et al. | |
| 2013/0235176 A1* | 9/2013 | Miyano | G02B 13/06 348/65 |
| 2014/0288417 A1 | 9/2014 | Schmidtlin et al. | |
| 2015/0025369 A1 | 1/2015 | Bhagavatula et al. | |
| 2015/0378105 A1 | 12/2015 | Godbout et al. | |
| 2016/0274345 A1 | 9/2016 | Ueno et al. | |
| 2016/0299170 A1 | 10/2016 | Ito et al. | |
| 2017/0168232 A1 | 6/2017 | Tearney et al. | |
| 2017/0235126 A1 | 8/2017 | DiDomenico | |
| 2018/0070932 A1 | 3/2018 | Tearney et al. | |
| 2018/0256032 A1 | 9/2018 | Takeuchi et al. | |
| 2019/0196188 A1* | 6/2019 | Hirata | G02B 27/0101 |
| 2019/0223700 A1 | 7/2019 | Elmaanaoui | |
| 2019/0227297 A1 | 7/2019 | Wu | |
| 2019/0227298 A1 | 7/2019 | Elmaanaoui | |

OTHER PUBLICATIONS

Eugene Hecht, Optics, 4th ed., Pearson Eduction, Adelphi University, 2002, pp. 261-264 (and title and copyright pages included) (The year of publication for this reference is sufficiently earlier than the effective U.S. filing date and any foreign priority date so that the particular month of publication is not in issue.).

Frank L. Pedrotti, et al., Introduction to Optics, 2nd ed, Prentice-Hall, Inc., Upper Saddle River, New Jersey, 1993, pp. 98-100 (and title and copyright pages included) (The year of publication for this reference is sufficiently earlier than the effective U.S. filing date and any foreign priority date so that the particular month of publication is not in issue.).

Yu-Kuan Lu et al., Asymmetric elliptic-cone-shaped microlens for efficient coupling to high-power laser diodes, Optics Express, vol. 15, No. 4, Feb. 19, 2007.

SPIE, Gradient Index Lens, Optipedia, Internet Archive Wayback Machine, May 16, 2016, downloaded from http://web.archive.org/web/20160516035942/http://spie.org/publications/tt48_55_gradient_index_lens.

Zhen Qiu et al., New Endoscopic Imaging Technology Based on MEMS Sensors and Actuators, Micromachines 2017, Jul. 2017.

Tianshi Wang et al., Numerical Analysis of Astigmatism Correction in Gradient Refractive Index Lens Based Optical Coherence Tomography Catheters, Applied Optics, 51(21):5244-5252, Jul. 20, 2012.

Woonggyu Jung et al., Numerical Analysis of Gradient Index Lens—Based Optical Coherence Tomography Imaging Probes, Journal of Biomedical Optics, vol. 15(6), Nov. 2010.

D. Yelin et al., Three-dimensional miniature endoscopy, Nature, Oct. 19, 2006, pp. 765—vol. 443.

* cited by examiner

OPTICAL PROBES WITH CORRECTION COMPONENTS FOR ASTIGMATISM CORRECTION

BACKGROUND

This application generally concerns optical probes.

An optical-imaging catheter or endoscope's optical system is usually fragile and is therefore protected by a sheath. Astigmatism is created in the optical system by the cylindrical shape of the sheath. Astigmatism causes the foci of the beams of light in two orthogonal directions to converge at different distances with different beam sizes or to diverge in one direction while converging in another direction. This astigmatism reduces the image quality of the optical system.

SUMMARY

Some embodiments of an optical probe comprise a light-guiding component, an optical component, a light-reflecting surface that is configured to receive light from the optical component and direct the light along a path, and a correction component. Also, the correction component lies in the path, the correction component has an optical power, and the correction component has a center of curvature that substantially coincides with an optical axis of the optical component.

Some embodiments of an optical probe comprise an optical fiber, a spacer, a lens, a light-reflecting component that is configured to receive light from the lens and direct the light along a path, and a correction component. The correction component includes a material that is at least partially transparent. Also, the correction component has an optical power in a sagittal direction, and the correction component lies along the path such that the light from the light-reflecting component travels through the material that is at least partially transparent.

Some embodiments of an optical probe comprise a lens, a light-reflecting component that is configured to receive light from the lens and direct the light along a path, and a correction component. The correction component has an optical power in a sagittal direction, and the correction component lies along the path such that correction component transmits the light from the light-reflecting component.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Some optical-imaging devices (e.g., endoscopes) are configured to capture images from inside a subject, such as a human patient. These optical-imaging devices may include an optical probe, and the optical probe may include both a lens and a reflecting surface at a distal tip. The lens and the reflecting surface focus a beam of light, collect the beam of light, and guide the beam of light. Also, one or more optical fibers in the fiber probe can be used to navigate the optical probe to a sample (e.g., organs, tissues), deliver light to the sample, and detect light that is reflected by the sample. Furthermore, an optical-imaging device may include a sheath that encloses the optical probe.

For example, an optical probe that is configured for optical coherence tomography (OCT) can capture depth-resolved images of blood vessels. As a beam of light from the optical probe is rotated across the surface, the optical probe can obtain cross-sectional images of the blood vessels in the surface. In order to acquire three-dimensional data, the optical probe can be translated longitudinally during the rotation to obtain images from a helical-scanning pattern. This helical scanning may be performed by pulling the tip of the optical probe back towards a proximal end while the optical probe is being rotated or by pushing the tip of the optical probe towards a distal end while the optical probe is being rotated.

The sheath may be a transparent or mostly-transparent sheath, through which a beam of light can travel. The sheath has an optical power, although the optical power of the sheath is not very strong when the medium inside and the medium outside the sheath are the same (e.g., the media inside and outside the sheath are both air) and the optical power from the sheath is negligible when the media inside and outside the sheath have refractive indices very close to the refractive index of the sheath (e.g. the media inside and outside the sheath are both a contrast agent that has a similar refractive index). However, if the media are different, then the sheath has a strong optical power. For example, if the medium inside the sheath is air and the medium outside the sheath is a contrast agent, then the sheath has a negative optical power in the sagittal direction. Additionally, the smaller the diameter of the sheath, the stronger the optical power of the sheath, and the greater the astigmatism caused by the sheath.

Figure 1:
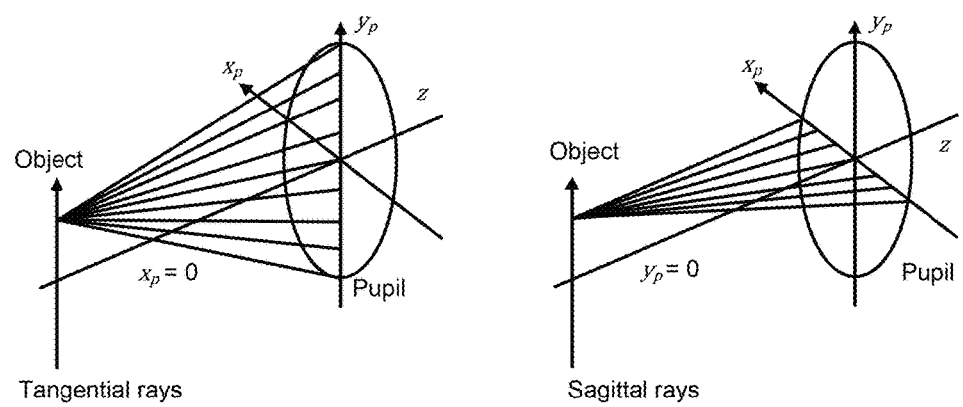
FIG. 1 illustrates ray definitions and a coordinate system.

FIG. 1 illustrates ray definitions and a coordinate system. Two sets of rays are used for astigmatism analysis: Tangential rays intersect the pupil at $x_p=0$, while sagittal rays intersect the pupil at $y_p=0$. The following description uses these ray definitions and this coordinate system.

Figure 2:
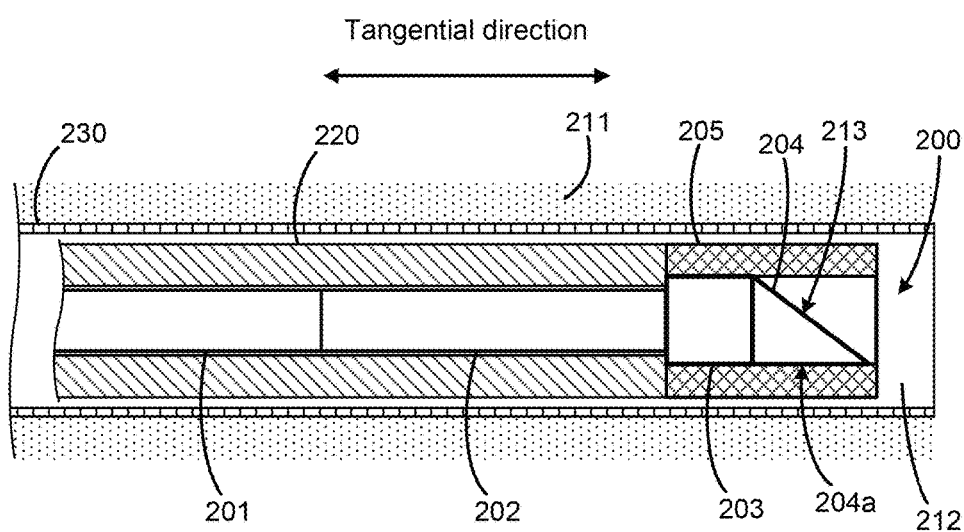
FIG. 2 illustrates a partially-cutaway view of an example embodiment of an optical-imaging device that includes an optical probe, a drive cable, and a sheath.

FIG. 2 illustrates a partially-cutaway view of an example embodiment of an optical-imaging device that includes an optical probe 200, a drive cable 220, and a sheath 230. The optical probe 200 includes a first light-guiding component 201 (e.g., single-mode optical fiber, multimode optical fiber, double-clad optical fiber), a second light-guiding component 202 (e.g., a glass rod), a lens 203 (e.g., a gradient-index (GRIN) lens), a light-reflecting component 204 (e.g., a prism), and a correction component 205 (e.g., a housing).

Also, some embodiments of the optical probe 200 include an optical component that includes the second light-guiding component 202 (e.g., a glass rod, a spacer), the lens 203, or a combination of the second light-guiding component 202 and the lens 203.

The light-reflecting component 204 has a light-reflecting surface 213, which reflects light, and an exiting surface 204a, where reflected light exits the light-reflecting component 204. Also, the sheath 230 contains an inner medium 212 (e.g., air, a contrast agent), which is the medium inside the sheath 230, and the sheath 230 is surrounded by an outer medium 211 (e.g., air, a contrast agent), which is the medium outside the sheath 230. The correction component 205 includes one or more transparent materials, and the correction component 205 has an optical power (e.g., a cylindrical surface that has an optical power). In some embodiments, the correction component 205 is a glass, plastic, sapphire, or epoxy tube.

One or more of the following can be designed to compensate for the astigmatism caused by the sheath 230: the curvature of the correction component 205, the refractive index of the correction component 205, the refractive index of a material (e.g., epoxy) between the light-reflecting component 204 and the correction component 205 (e.g., see FIG. 7), and the curvature of the exiting surface 204a of the light-reflecting component 204. The drive cable 220 and the optical probe 200 are fixed relative to each other. The drive cable 220 delivers torque from a proximal end to a distal end in order to spin the distal end, which is attached to the optical probe 200. Spinning the optical probe 200 permits the optical probe to capture a 360° view.

Figure 3:
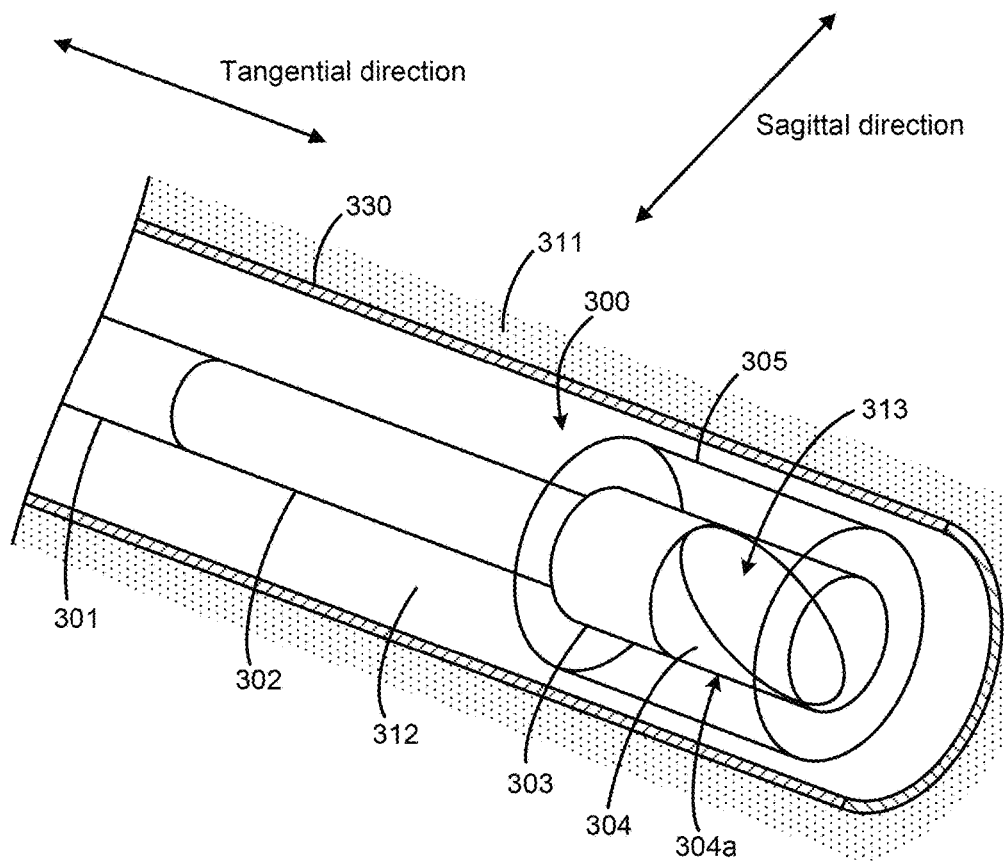
FIG. 3 illustrates a perspective, partially-cutaway view of an example embodiment of an optical-imaging device that includes an optical probe and a sheath.

FIG. 3 illustrates a perspective, partially-cutaway view of an example embodiment of an optical-imaging device that includes an optical probe and a sheath. The optical probe 300 includes a first light-guiding component 301, a second light-guiding component 302, a lens 303, a light-reflecting component 304, and a correction component 305. The correction component 305 has an optical power (e.g., a cylindrical surface).

Because the sheath 330 has an asymmetric optical power, the sheath 330 can cause astigmatism. For example, the sagittal optical power of the sheath is negative if $$(n_{sheath} - n_i) > \frac{R_{Si}}{R_{So}}(n_{sheath} - n_{ca}),$$

where $n_{sheath}$ is the refractive index of the sheath 330, where $n_i$ is the refractive index of the inner medium 312 (e.g., air, a contrast agent), and where $n_{ca}$ is the refractive index of the outer medium 311 (e.g., a contrast agent, water, saline). Also, $R_{Si}$ is the inner radius of the sheath 330, and $R_{So}$ is the outer radius of the sheath 330. Thus, in embodiments where $n_{sheath}=1.5$, where $R_{Si}/R_{So}<1$, where either $n_i=1$ for air or $n_i=1.3$-$1.45$ for epoxy, and where $n_{ca}=1.45$, the above equation is satisfied (the sheath has negative power).

The first light-guiding component 301 and the second light-guiding component 302 can deliver beams of light in two different wavelengths to the distal tip of the optical probe 300. One wavelength may be used for OCT, and in some embodiments the wavelength is 1310 nm. The wavelength can be broadband or, alternatively, can be scanned for a bandwidth of about 100 nm to 150 nm. The other wavelength may be a wavelength of excitation for fluorescence, for example 633 nm.

The first light-guiding component 301 may be, for example, a double-clad fiber or a single mode fiber. The second light-guiding component 302 may be, for example, a glass rod or another spacer that can be used to adjust the numerical aperture (NA) of a beam of light to the entrance of the lens 303. The lens 303 may be a GRIN lens that is attached to a proximal end of the light-reflecting component 304. The light-reflecting component 304 has a light-reflecting surface 313, which may have a total internal reflection (TIR) or a mirror-coated surface. Light exits the light-reflecting component 304 from an exiting surface 304a, which may be a flat surface or a curved surface. In some embodiments, the curvature of the exiting surface 304a of the light-reflecting component 304 matches the outer diameter of the lens 303, which may provide easier mechanical assembly, robust connection, or improved optical-collection efficiency.

After light exits the light-reflecting component 304, the light passes through the correction component 305. In this embodiment, the center of curvature of the correction component 305 substantially coincides with an optical axis of the lens 303, an optical axis of the second light-guiding component 302, or an optical axis of the first light-guiding component 301. For example, in some embodiments, the center of curvature of the correction component 305 substantially coincides with the optical axis the first light-guiding component 301 if the center of curvature of the correction component 305 is offset from the optical axis of the first light-guiding component 301 by approximately +−10% of the outer radius of curvature of the correction component 305 (e.g., for a correction component 305 that has an outer diameter of 500 um, the acceptable error range from the optical axis of the first light-guiding component 301 would be about +−50 um). Also, the correction component 305 has an optical power (e.g., an optical power only in the sagittal direction) that provides a correction to the astigmatism that is produced by the sheath 330 and the exiting surface 304a of the light-reflecting component 304. In the embodiment that is shown in FIG. 3, the astigmatism of the OCT beam at the wavelength of 1310 nm is at least partially corrected at a focus point.

For example, assuming that the outer medium 311 is a contrast agent and the inner medium 312 is air, then in the sagittal direction, a cylindrical exiting surface 304a of the light-reflecting component 304 has a positive optical power, while the correction component 305 and the sheath 330 each have a negative optical power. The exiting surface 304a has an absolute optical power that is stronger than the individual absolute optical powers of the correction component 305 and the sheath 330. The refractive indices, the radius of the light-reflecting component 304, the radii (inner and outer) of the correction component 305, the radii (inner and outer) of the sheath 330, and the gaps between each member are designed such that the sagittal optical powers of the light-reflecting component 304, the correction component 305, and the sheath 330 compensate for each other in the sagittal direction, for example as described by the following:

$$\phi_{prism} + \phi_{correction\ element} + \phi_{sheath} = 0,$$

$$\phi_{sheath} < 0,$$

$$\phi_{prism} > 0, \text{ and}$$

$$\phi_{correction\ element} < 0,$$

where $\phi_{prism}$ is the sagittal optical power of the exiting surface 304a of the light-reflecting component 304, where $\phi_{correction\ element}$ is the sagittal optical power of the correction component 305, and where $\phi_{sheath}$ is the sagittal optical power of the sheath 330. In some embodiments, the astigmatism is not perfectly corrected but is controlled (the astigmatism is not zero but is close to zero).

In some embodiments, the astigmatism correction and the control of the beam-waist location (the working distance) are accomplished by properly configuring the dimensions of the second light-guiding component 302, the dimensions and the refractive index of the lens 303, the dimensions and the refractive index of the light-reflecting component 304, and the dimensions of the correction component 305. The dimensions include the radii of the curvature of the cylindrical surfaces and include the lengths of these members. Also, the materials that compose the members and the inner medium 312 (e.g., the refractive index of the inner medium 312) may be used to implement the astigmatism correction.

Some embodiments of the optical probe 300 are configured for a multimodality system that simultaneously performs OCT imaging using light with a wavelength of 1.31 um and fluorescence mapping using light with a wavelength of 0.633 um. Depending on the specification of the imaging, it may be critical to focus the OCT wavelength, which can provide structural information, at a designed optimal working distance to provide lateral resolution, while the fluorescence wavelength is focused slightly off from the optimal working distance of the OCT imaging, thereby allowing the fluorescence wavelength to have a larger beam size with a lower lateral resolution at the optimal working distance of the OCT imaging.

For example, in coronary arteries, the diameters of the arteries of interest are often about 2 to 4 mm. Assuming that the optical probe 300 is located at the center of the artery, the radius of the artery corresponds to the working distance, and is 1 to 2 mm from the optical axis of the optical probe 300.

OCT and fluorescence wavelengths both penetrate the vessel, so, in some embodiments, the focus position or the working distance is optimal at 1 to 3 mm. Within these working distances, the focus may be different between the two modalities. For example, the embodiments in FIGS. 5 and 9 have OCT and fluorescence focal distances that are within 0.5 mm of each other. Some embodiments of the optical probe 300 (e.g., for coronary-artery measurement) have focal distances or working distances that are within 2 mm of each other. Some embodiments have larger differences in the focal distances or working distances, for example embodiments that are used for larger blood vessels (e.g., peripheral arteries), corresponding to the blood vessel's diameter and the desired working distance.

The optimization of the focal point may be accomplished by using the refractive indices for the two wavelengths and solving the optimization problem. When optimizing, it may be efficient to add another material, with a different combination of refractive indices for the two wavelengths, by splitting one or more optical components or by adding a spacer.

Also, some embodiments of the optical probe 300 are configured for other modalities, such as near-infrared spectroscopy, in addition to or in alternative to OCT and fluorescence imaging.

Figure 4:
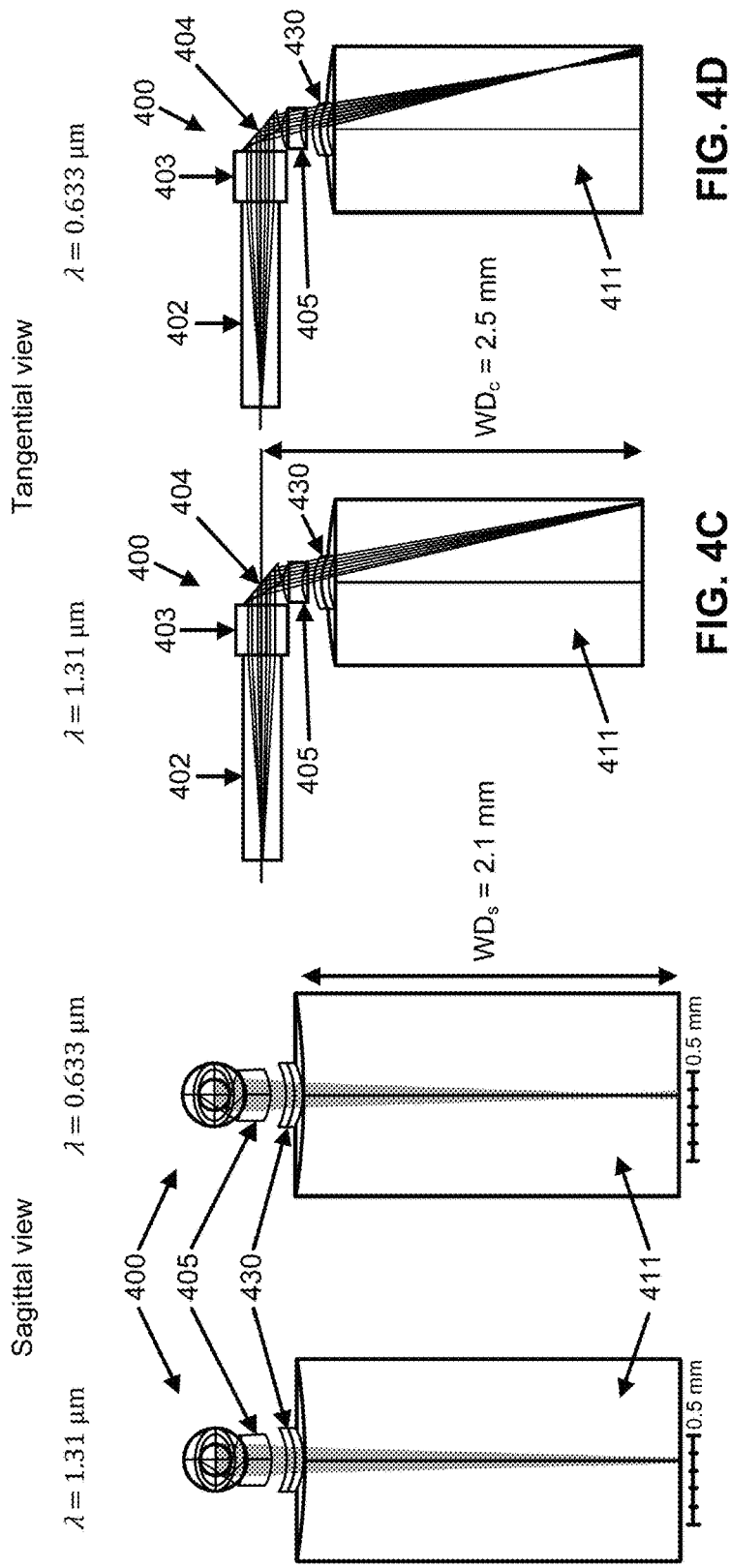
FIGS. 4A-D illustrate sagittal views and tangential views of an example embodiment of an optical-imaging device that includes an optical probe and a sheath.

FIGS. 4A-D illustrate sagittal views and tangential views of an example embodiment of an optical-imaging device that includes an optical probe and a sheath. FIGS. 4A and 4C show the transmission of light that has a wavelength λ of 1.31 μm (λ=1.31 μm) by the optical probe 400 and the sheath 430, and FIGS. 4B and 4D show the transmission of light that has a wavelength λ of 0.633 μm (λ=0.633 μm) by the optical probe 400 and the sheath 430. In this embodiment, light travels through a second light-guiding component 402, which is a 1.4 mm long coreless fused-silica rod in this embodiment, and then travels through a lens 403, which is a GRIN lens in this embodiment. Next, the light is reflected by a light-reflecting surface of a light-reflecting component 404. The light then travels through an exiting surface of the light-reflecting component 404 (which has an optical power only in the sagittal direction), then travels through a correction component 405, and then travels through the sheath 430, which has an optical power only in the sagittal direction. After traveling through the sheath 430, the light travels through a contrast agent 411, and the contrast agent's refractive index is 1.45 (n=1.45).

In this example embodiment, the lens 403 has diameter of 0.35 mm. The optical parameters of the lens 403 are listed below in Table 1:

TABLE 1

Optical parameters of the lens

| | Square root of A | Refractive index at the center |
|---|---|---|
| Wavelength: 0.550 μm | 1.71 | 1.643 |

In this example embodiment, the light-reflecting component 404 is a prism that has a refractive index of 1.36 and a tilt angle such that the chief ray of light from the lens 403 has an incident angle of approximately 50°. The light-exiting surface of the light-reflecting component 404 has a radius of 0.35 mm (convex) in the sagittal direction, which matches the outer diameter of the lens 403. Also, there is a 10 μm air gap between the exiting surface of the light-reflecting component 404 and the inner surface of the correction component 405. The gap could be filled with another optically-transparent material, such as epoxy, if proper adjustments are made to the radius and the refractive index of the correction component 405. The correction component 405 has an inner radius of 0.18 mm and an outer radius of 0.25 mm, and the correction component 405 is composed of BK7 glass. Additionally, the sheath 430 has an inner diameter of approximately 0.600 mm, a thickness of 0.1 mm, and a refractive index of 1.5. In the tangential direction, the chief ray of light has an incident angle to the sheath 430 that is approximately 20° in air.

The astigmatism of the OCT beam at the wavelength λ of 1.31 μm (λ=1.31 μm) is corrected at a focus point that is 2.5 mm away from the optical axis of the lens 405, and the focus point is also 2.1 mm away from the outer diameter of the sheath 430. Accordingly, the working distance $WD_s$ from the outer diameter of the sheath 430 is 2.1 mm, and the working distance $WD_c$ from the optical axis of the lens 403 is 2.5 mm.

Figure 5:
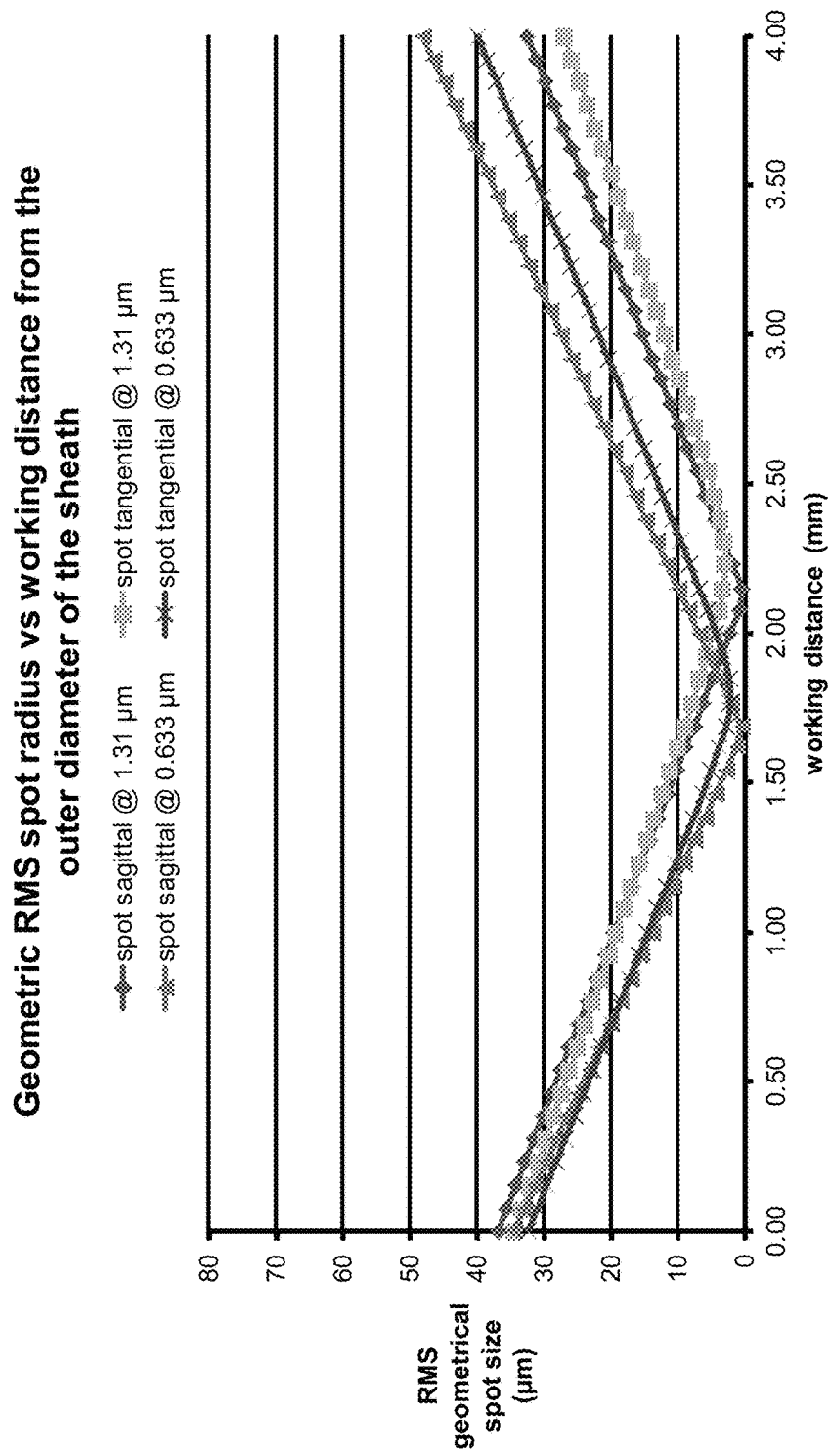
FIG. 5 illustrates the root mean square (RMS) of the geometrical optical spot radius versus the working distance from the outer diameter of the sheath for the example embodiment of an optical-imaging device that is illustrated in FIGS. 4A-D.

FIG. 5 illustrates the root mean square (RMS) of the geometrical optical spot radius versus the working distance from the outer diameter of the sheath for the example embodiment of an optical-imaging device that is illustrated in FIGS. 4A-D. FIG. 5 indicates that, in both the tangential and the sagittal directions, the beams of light in the 1.31 μm wavelength focus at approximately the same distance (2.1 mm) from the outer sheath.

Figure 6:
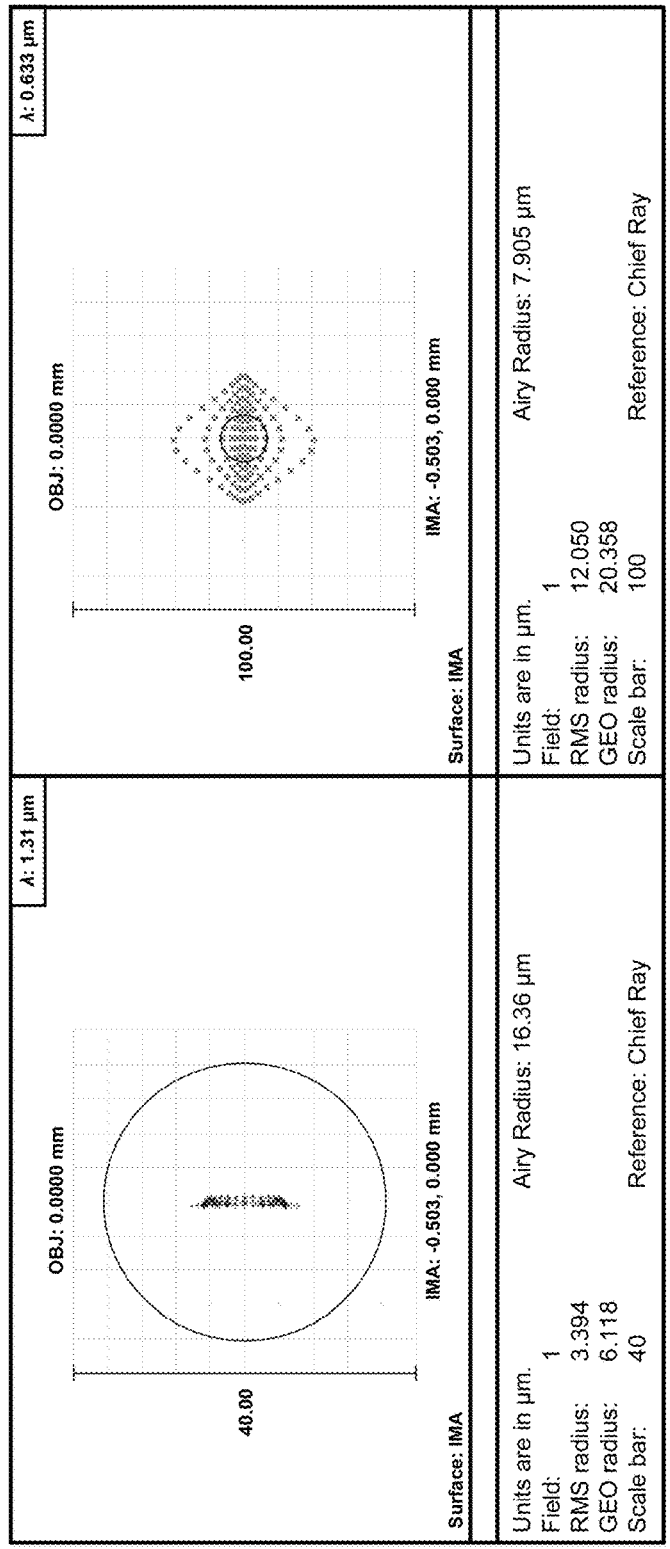
FIG. 6 illustrates the geometrical spot radii at the $\lambda=1.31$ μm and the $\lambda=0.633$ μm wavelengths at a focus point that is 2.5 mm away from an optical axis of the lens for the example embodiment of an optical-imaging device that is illustrated in FIGS. 4A-D.

FIG. 6 illustrates the geometrical spot radii at the λ=1.31 μm and the λ=0.633 μm wavelengths at a focus point that is 2.5 mm away from an optical axis of the lens in the example embodiment of an optical-imaging device that is illustrated in FIGS. 4A-D. The diffraction limit has a 16.36 μm Airy radius in the wavelength λ of 1.31 μm (λ=1.31 μm) and has a 7.9 μm Airy radius in the wavelength λ of 0.633 μm (λ=0.633 μm). The RMS spot radius at the wavelength λ of 0.633 μm (λ=0.633 μm) is 12.051 μm, mainly due to chromatic focal shift.

Figure 7:
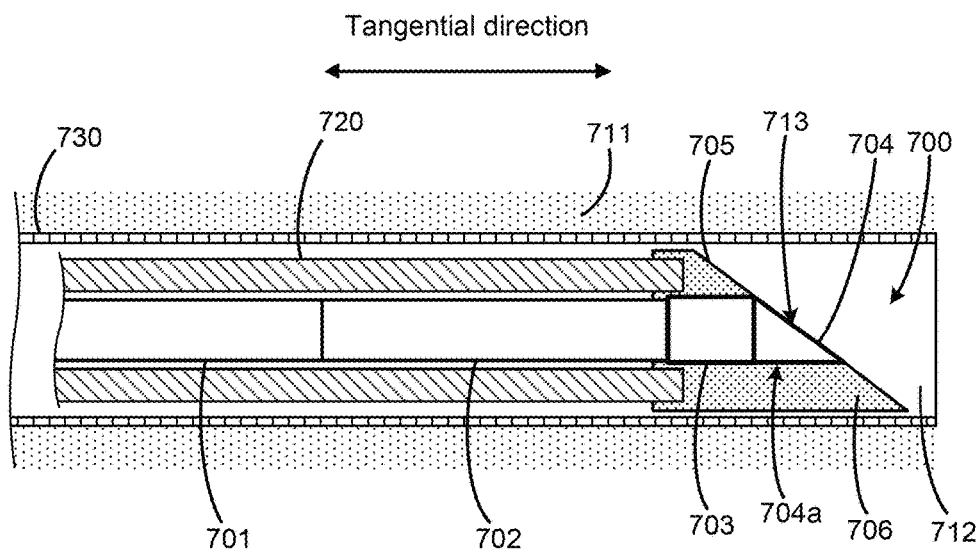
FIG. 7 illustrates a partially-cutaway view of an example embodiment of an optical-imaging device that includes an optical probe, a drive cable, and a sheath.

FIG. 7 illustrates a partially-cutaway view of an example embodiment of an optical-imaging device that includes an optical probe, a drive cable, and a sheath. The optical probe 700 is surrounded by an inner medium 712, which is contained in the sheath 730, and the sheath 730 is surrounded by an outer medium 711. The optical probe 700 includes a first light-guiding component 701; a second light-guiding component 702; a lens 703; a light-reflecting component 704, which includes a light-reflecting surface 713 and an exiting surface 704a; and a correction component 705. In this embodiment, the correction component 705 is an optically-transparent tube (e.g., a heat-shrink tube) that is filled with epoxy 706 or another suitable adhesive 706. The epoxy 706 (or other adhesive 706) is at least partially transparent. The drive cable 720 is affixed to the lens 703 and the correction component 705 by the epoxy 706 (or other adhesive 706). In some embodiments, the correction component 705 has been angle-polished to create a total-internal reflection (TIR) surface, such that the light that exits the correction component 705 then enters the sheath 730 with an incident angle that is between 10° and 30° (e.g., approximately 20°).

In the sagittal direction, the surface of the correction component 705 has a positive optical power, while the sheath 730 has a negative optical power. The refractive indices of the members, as well as the radii of the correction component 705 and the sheath 730, are configured such that the sagittal optical powers of the correction component 705 and the sheath 730 essentially cancel each other. In some embodiments, the sagittal optical powers of the correction component 705 and the sheath 730 can be described by the following:

$$\phi_{correction\ element} + \phi_{sheath} = 0, \text{ and}$$

$$\phi_{sheath} < 0,$$

where $\phi_{correction\ element}$ is the sagittal optical power of the correction component 705, and where $\phi_{sheath}$ is the sagittal optical power of the sheath 730.

Figure 8:
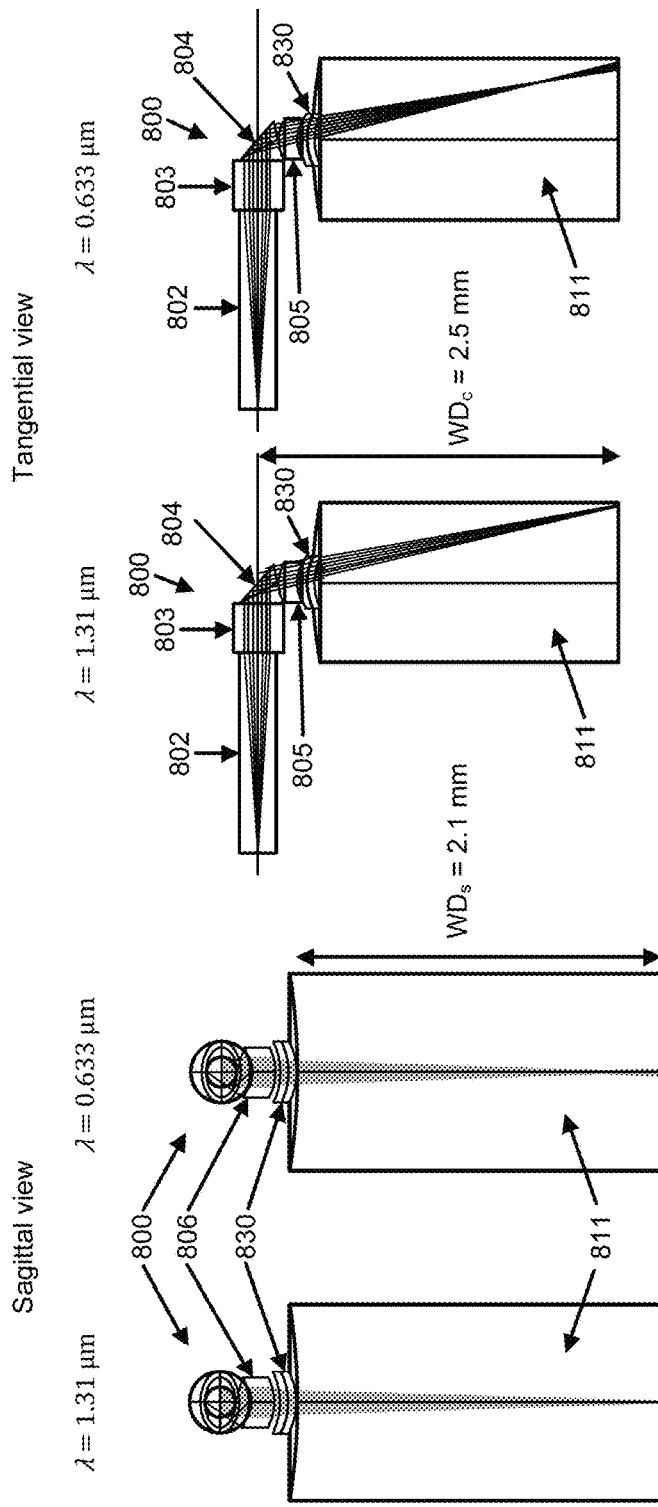
FIGS. 8A-D illustrate sagittal views and tangential views of an example embodiment of an optical-imaging device that includes an optical probe and a sheath.

FIGS. 8A-D illustrate sagittal views and tangential views of an example embodiment of an optical-imaging device that includes an optical probe and a sheath. FIGS. 8A and 8C show the transmission of light that has a wavelength λ of 1.31 μm (λ=1.31 μm) by the optical probe and the sheath, and FIGS. 8B and 8D show the transmission of light that has a wavelength λ of 0.633 μm (λ=0.633 μm) by the optical probe and the sheath. Light travels through a second light-guiding component 802, which is a 1.4 mm long coreless fused-silica rod in this example embodiment. The light then travels through a lens 803, which is a GRIN lens that has a length of 0.35 mm. Next, the light is reflected by a light-reflecting component 804 or by a light-reflecting surface that was created by angle polishing the correction component 805 with a tilt angle, for example an angle of approximately 50°, and then the light travels through the correction component 805, which has a refractive index of 1.4. For example, the correction component 805 may be a tube that is filled with epoxy, and the light-reflecting component 804 can be a prism that is immersed in the epoxy. The light-reflecting component 804 can also be an integral part of the epoxy, and, in these embodiments, the light is reflected by an angle-polished surface in the epoxy.

Then the light exits the correction component 805 and travels through the sheath 830. The correction component 805 has an inner diameter of 0.35 mm, an outer diameter of 0.550 mm, and a thickness of approximately 0.1 mm. The sheath 830 has an inner diameter of approximately 0.6 mm and a thickness of approximately 0.1 mm. There is an air gap of approximately 25 μm between the outer diameter of the correction component 805 and the inner surface of the sheath 830. Also, the chief-ray incident angle to the sheath 830 is about 20° in the air, and the correction component 805 and the sheath 830 each have an optical power only in the sagittal direction. After traveling through the sheath 830, the light travels through a contrast agent 811, and the contrast agent's refractive index is 1.45 (n=1.45). In this example, the working distance is 2.5 mm from the optical axis of the lens 803 and is 2.1 mm from the outer diameter of the sheath 830.

Figure 9:
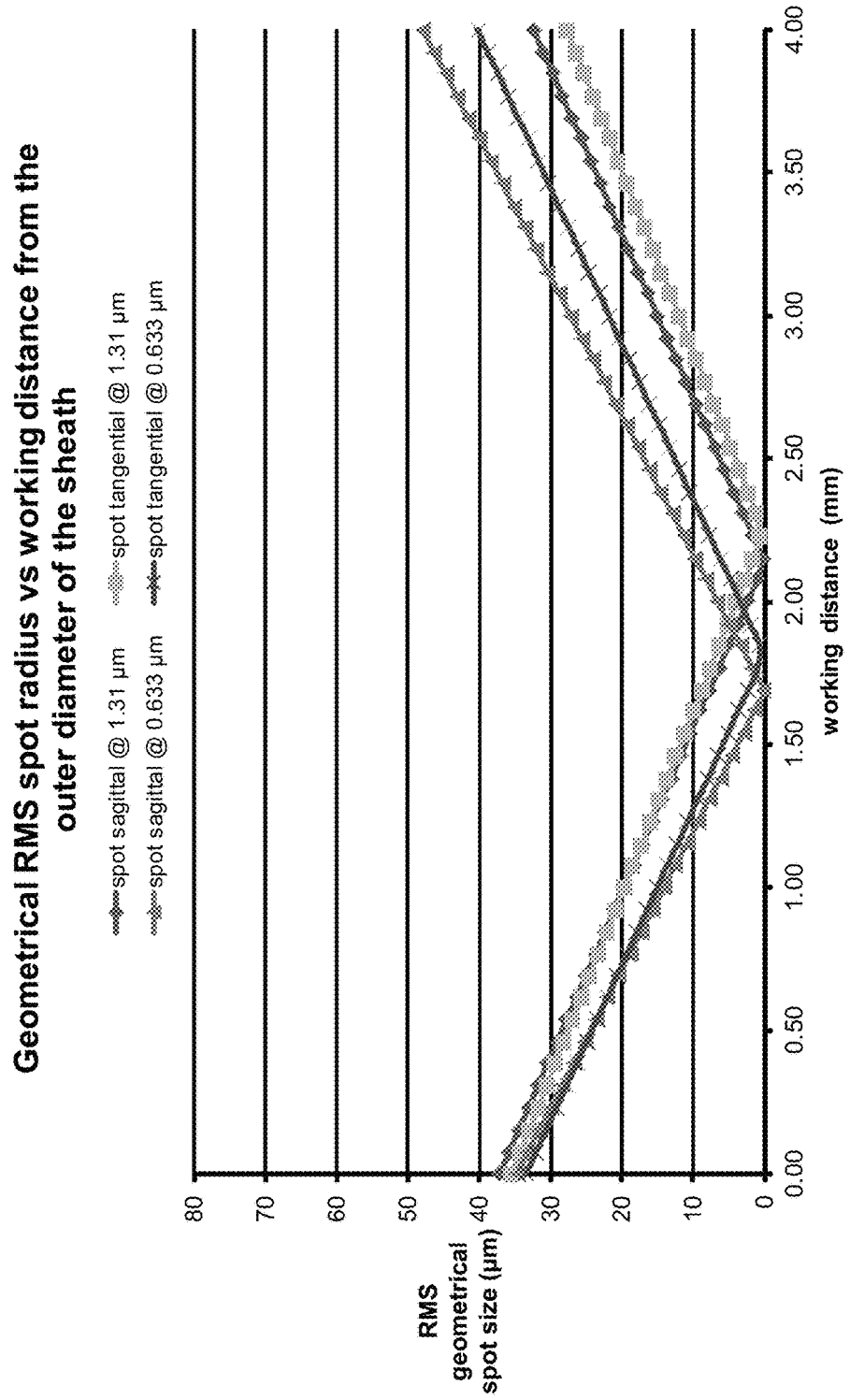
FIG. 9 illustrates the root mean square (RMS) of the geometrical optical spot radius versus the working distance from the outer diameter of the sheath for the example embodiment of an optical-imaging device that is illustrated in FIGS. 8A-D.

FIG. 9 illustrates the root mean square (RMS) of the geometrical optical spot radius versus the working distance from the outer diameter of the sheath for the example embodiment of an optical-imaging device that is illustrated in FIGS. 8A-D. FIG. 9 indicates that, in both the tangential and the sagittal directions, the beams of light in both the 1.31 μm wavelength and the 0.633 μm wavelength focus at approximately the same distance (2.1 mm) from the outer sheath.

Figure 10:
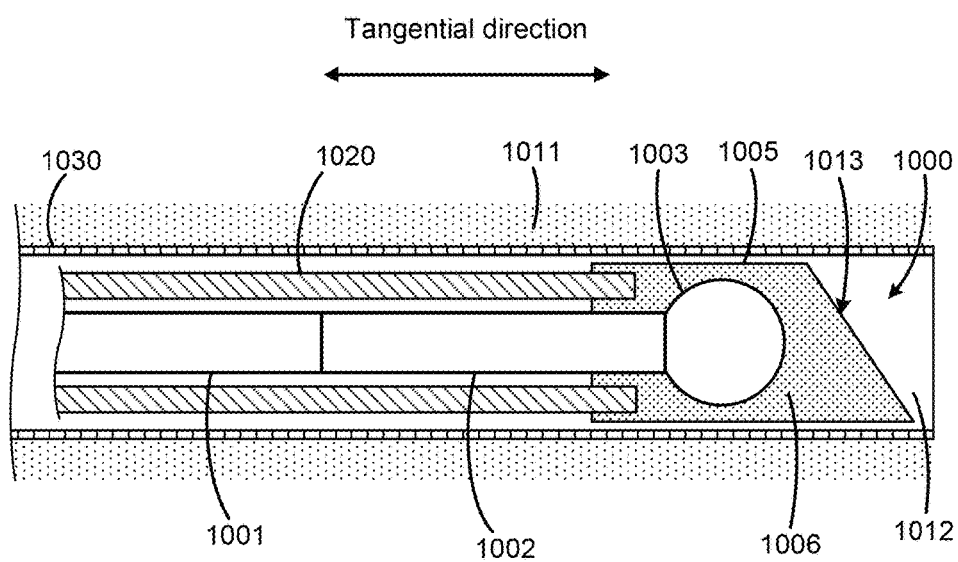
FIG. 10 illustrates a partially-cutaway view of an example embodiment of an optical-imaging device that includes an optical probe, a drive cable, and a sheath.

FIG. 10 illustrates a partially-cutaway view of an example embodiment of an optical-imaging device that includes an optical probe, a drive cable, and a sheath. The optical probe 1000 is surrounded by an inner medium 1012, which is contained in the sheath 1030, and the sheath 1030 is surrounded by an outer medium 1011. The optical probe 1000 includes a first light-guiding component 1001, a second light-guiding component 1002, a ball lens 1003 (e.g., a glass ball lens, a sapphire ball lens), and a correction component 1005. The correction component 1005 is an optically-transparent tube (e.g., a polymer tube, a heat-shrink tube, a glass tube, or a sapphire tube) that may be filled with epoxy or another suitable adhesive. In the example embodiment in FIG. 10, the correction component 1005 is filled with epoxy 1006. The epoxy 1006 (or other adhesive) is at least partially transparent. The drive cable 1020 is affixed to the ball lens 1003 and the correction component 1005, for example by the epoxy 1006. In this embodiment, the correction component 1005 is filled with epoxy 1006 and has been angle-polished to create a light-reflecting surface 1013 (e.g., a TIR surface) such that the light that exits the correction component 1005 and then enters the sheath 1030 has an incident angle of approximately 20°. Thus, in this embodiment, the correction component 1005 is also a light-reflecting component.

Also for example, in some embodiments, the ball lens 1003 is formed from shaping an end of the second light-guiding component 1002 (e.g., a fused-silica coreless fiber, a glass rod, a sapphire coreless fiber, a sapphire rod) into the ball lens 1003 by fusion splicing, and the first light-guiding component 1001 is spliced to the other end of the second light-guiding component 1002. Also, in some embodiments the ball lens 1003 is attached to the second light-guiding component 1002 by epoxy or another adhesive. In such embodiments, although any type of ball lens can be used, a higher refractive index of the ball lens 1003 (e.g., a sapphire ball lens) may produce better optical performance.

In the sagittal direction, the cylindrical surface of the correction component 1005 has a positive optical power, while the sheath 1030 has a negative optical power. The refractive indices, as well as the radii, of the correction component 1005 and the sheath 1030 are configured such that the sagittal optical powers of the correction component 1005 and the sheath 1030 compensate for each other (e.g., cancel each other). In some embodiments, the sagittal optical powers of the correction component 1005 and the sheath 1030 can be described by the following:

$$\phi_{correction\ element} + \phi_{sheath} = 0, \text{ and}$$

$$\phi_{sheath} < 0,$$

where $\phi_{correction\ element}$ is the sagittal optical power of the correction component 1005, and where $\phi_{sheath}$ is the sagittal optical power of the sheath 1030.

Figure 11:
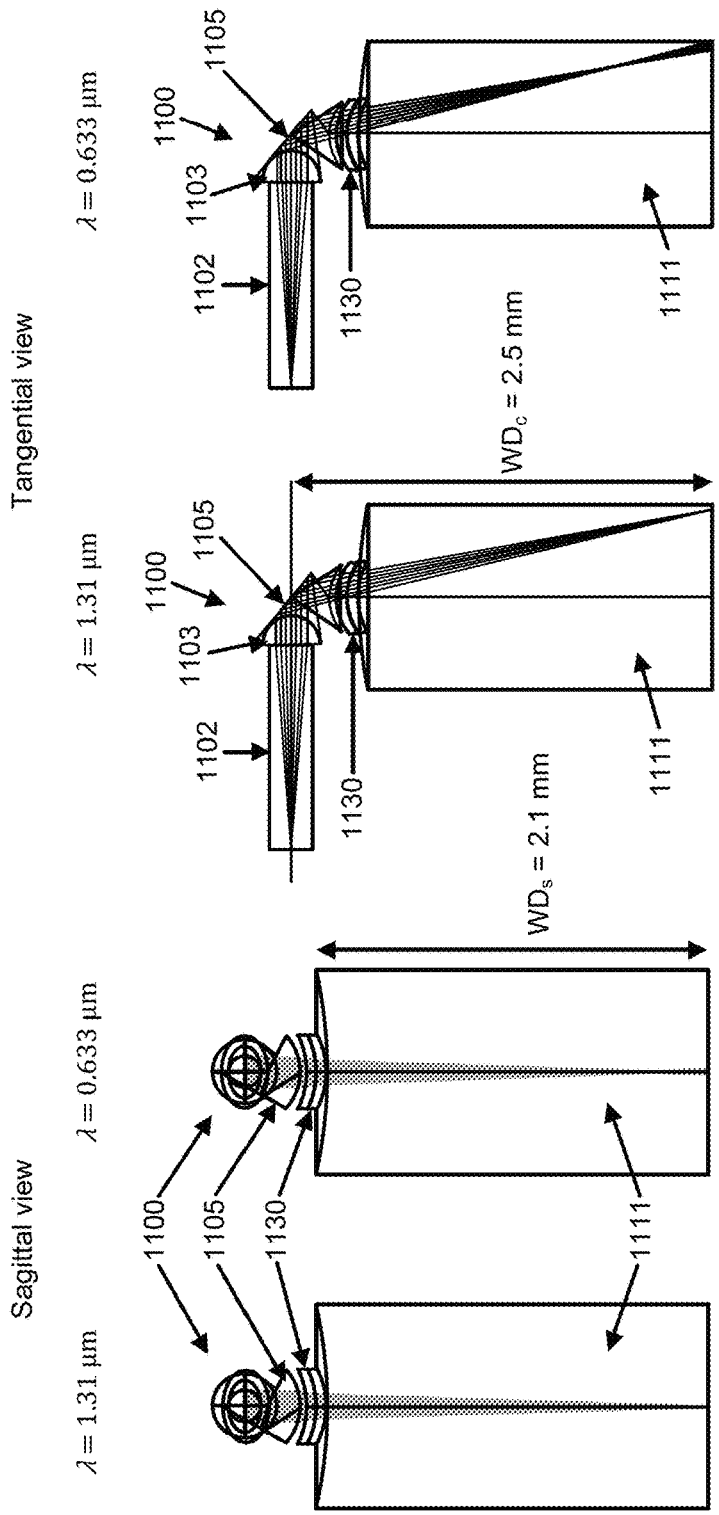
FIGS. 11A-D illustrates sagittal views and tangential views of an example embodiment of an optical-imaging device that includes an optical probe and a sheath.

FIGS. 11A-D illustrate sagittal views and tangential views of an example embodiment of an optical-imaging device that includes an optical probe and a sheath. FIGS. 11A and 11C show the transmission of light that has a wavelength λ of 1.31 μm (λ=1.31 μm) by the optical 1100 probe and the sheath 1130, and FIGS. 11B and 11D show the transmission of light that has a wavelength λ of 0.633 μm (λ=0.633 μm) by the optical probe 1100 and the sheath 1130. Light travels through a second light-guiding component 1102, which is a 1.2 mm long coreless double-clad fiber in this example embodiment. The light then enters a ball lens 1103, which is a ball lens that has a radius of 175 μm and a refractive index of 1.68. Next, the light travels through a correction component 1105, which is a tube filled with a transparent adhesive that has a refractive index of 1.4, and the light is reflected by a light-reflecting surface that was created by angle polishing the correction component 1105 with a tilt angle of approximately 50°. Then the light exits the correction component 1105 through a cylindrical surface, and the light travels through the sheath 1130. After traveling through the sheath 1130, the light travels through a contrast agent 1111, and the contrast agent's refractive index is 1.45.

The length of the second light-guiding component 1102, the radius of the ball lens 1103, the material of the ball lens 1103, the length of the correction component 1105, the radius of the correction component 1105, and the material of the correction component 1105 are selected and configured such that the astigmatism in the optical system is corrected and the beam is focused at the desired working distance, and they may be selected so that other aberrations in the optical system are also corrected. In this example embodiment, the correction component 1105 has a radius of 0.270 mm. Also, the sheath 1130 has an inner diameter of 0.6 mm and a thickness of approximately 0.1 mm. And there is an air gap of approximately 30 μm between the outer diameter of the correction component 1105 and the inner surface of the sheath 1130. In this example, the working distance is 2.5 mm from the optical axis of the lens 1003 and is 2.1 mm from the outer diameter of the sheath 1030.

Additionally, the ball lens 1103 can be fastened (e.g., epoxied) to the second light-guiding component 1102, although in some embodiments the ball lens 1103 is directly formed from the second light-guiding component 1102.

Figure 12:
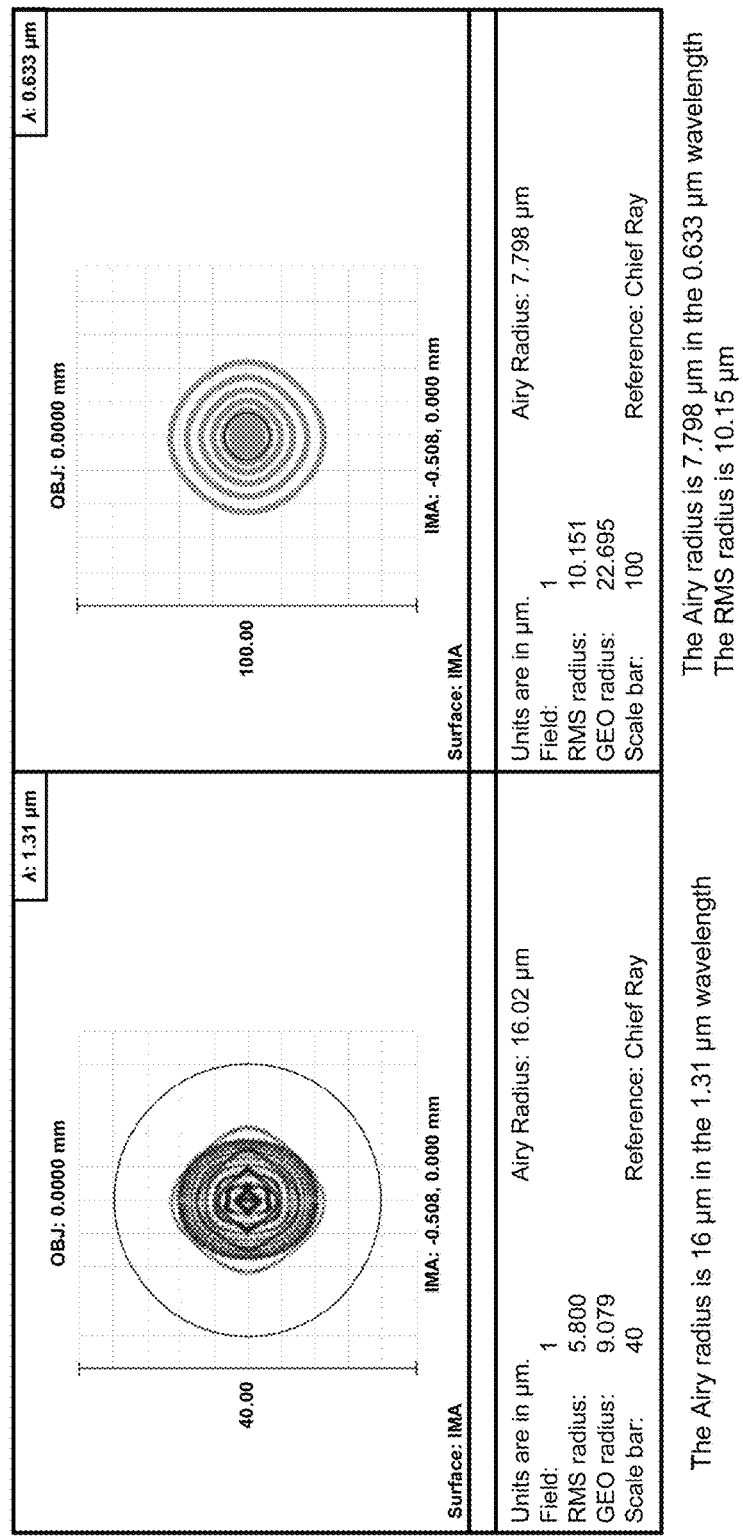
FIG. 12 shows the geometrical spot radii at the $\lambda=1.31$ μm and the $\lambda=0.633$ μm wavelengths at a focus point that has a vertical distance of 2.5 mm from the optical axis of the lens for the example embodiment of an optical-imaging device that is illustrated in FIGS. 11A-D.

FIG. 12 shows the geometrical spot radii at the λ=1.31 μm and the λ=0.633 μm wavelengths at a focus point that has a vertical distance of 2.5 mm from the optical axis of the lens for the example embodiment of an optical-imaging device that is illustrated in FIGS. 11A-D. The diffraction limit has a 16.02 μm Airy radius in the wavelength λ of 1.31 μm (λ=1.31 μm) and has a 7.798 μm Airy radius in the wavelength λ of 0.633 μm (λ=0.633 μm). The RMS spot radius is 10.2 μm in the wavelength λ of 0.633 μm (λ=0.633 μm).

Figure 13:
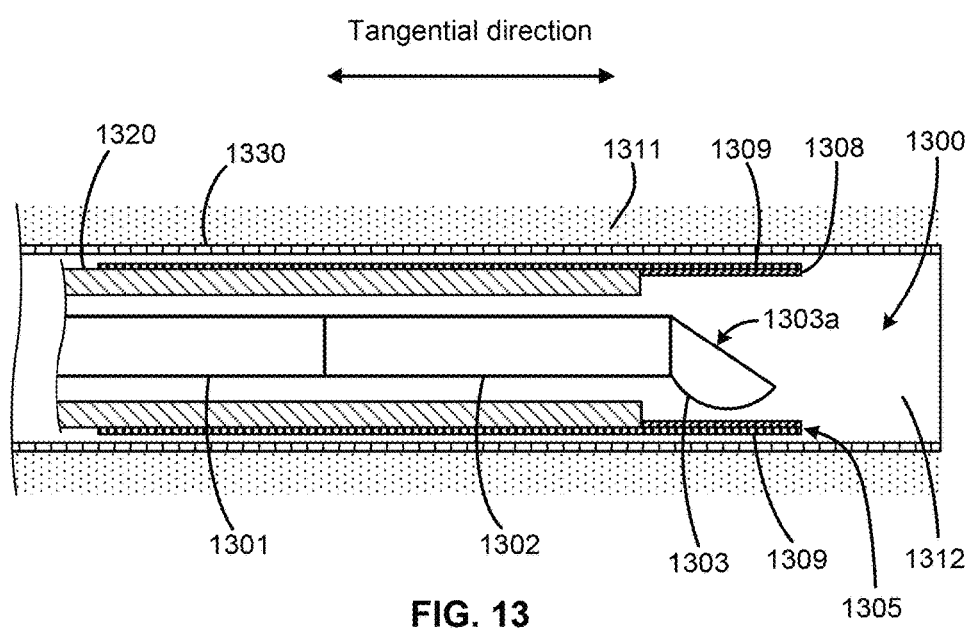
FIG. 13 illustrates a partially-cutaway view of an example embodiment of an optical-imaging device that includes an optical probe, a drive cable, and a sheath.

FIG. 13 illustrates a partially-cutaway view of an example embodiment of an optical-imaging device that includes an optical probe, a drive cable, and a sheath. The drive cable 1320 is attached to the optical probe 1300. The optical probe 1300 is surrounded by an inner medium 1312, which is contained in the sheath 1330, and the sheath 1330 is surrounded by an outer medium 1311. The optical probe 1300 includes a first light-guiding component 1301, a second light-guiding component 1302, a ball lens 1303, and a correction component 1305. The correction component 1305 includes an inner tube 1308 and an outer tube 1309.

In this embodiment, the inner tube 1308 and the outer tube 1309 compose a double-layer tube. However, some embodiments of the correction component 1305 do not include a double-layer tube, and instead include just one of the inner tube 1308 and the outer tube 1309. Also, in some embodiments, the inner tube 1308 and the outer tube 1309 are each made of one or more of the following: glass, plastics, and polymers. The inner tube 1308 may contain epoxy or another fluid such that the refractive index between the ball lens 1303 and the inner tube 1308 is not 1.

The ball lens 1303 may be formed from the same piece as the second light-guiding component 1302 and then angled polished to form a light-reflecting surface 1303a. For example, the light-reflecting surface 1303a may have an angle such that the incident angle of an exiting beam of light to the normal of the sheath 1330 is approximately 20°.

After a beam of light is reflected by the angled light-reflecting surface 1303a of the ball lens 1303, the beam of light is focused by the curvature of the ball lens 1303 and passes through the inner tube 1308 and the outer tube 1309. The double-layer correction component 1305, which is composed of the inner tube 1308 and the outer tube 1309, is at least partially optically transparent and has an optical power in the sagittal plane that compensates for the optical power of the sheath 1330.

Figure 14:
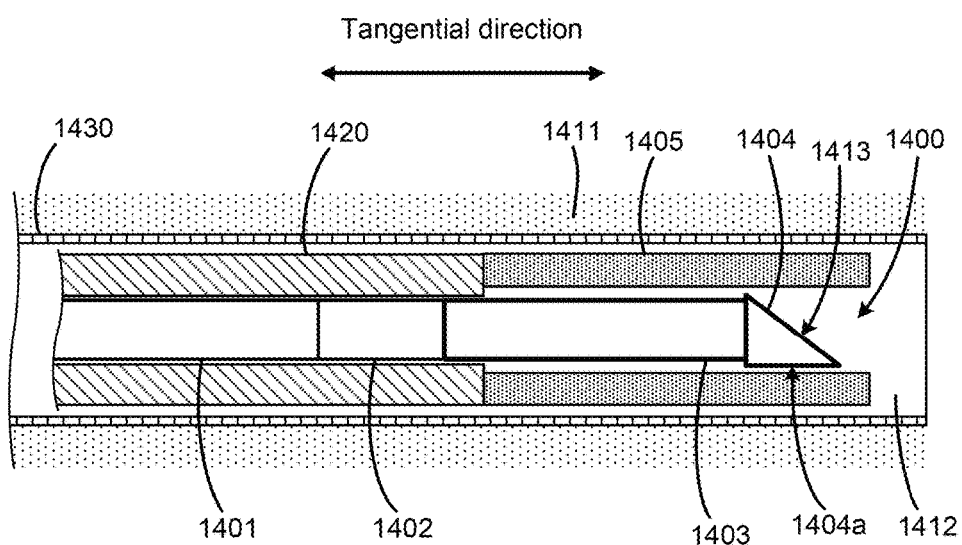
FIG. 14 illustrates a partially-cutaway view of an example embodiment of an optical-imaging device that includes an optical probe, a drive cable, and a sheath.

FIG. 14 illustrates a partially-cutaway view of an example embodiment of an optical-imaging device that includes an optical probe, a drive cable, and a sheath. The drive cable 1420 is attached to the optical probe 1400. The optical probe 1400 is surrounded by an inner medium 1412, which is contained in the sheath 1430, and the sheath 1430 is surrounded by an outer medium 1411. The optical probe 1400 includes a first light-guiding component 1401, a second light-guiding component 1402, a lens 1403, a correction component 1405, and a light-reflecting component 1404. The light reflecting-component 1404 includes a light-reflecting surface 1413 and an exiting surface 1404a. Also, the correction component 1405 is made of one or more transparent materials, for example glass or sapphire. A sapphire tube has a high refractive index (~1.78) and, in some circumstances, may provide a better astigmatism correction than some other materials. The curvatures and the refractive index of the correction component 1405, the refractive index and the curvature of the exiting surface 1404a of the light-reflecting component 1404, and the inner medium 1412 (e.g., air, epoxy) are configured to compensate for the aberrations that are caused by the sheath 1430. For example, the negative power of the correction component 1405 (e.g., a sapphire tube, a glass tube) plus the negative power of the sheath 1430 plus the positive power of the light-reflecting component 1404 may approximately equal zero.

Figure 15:
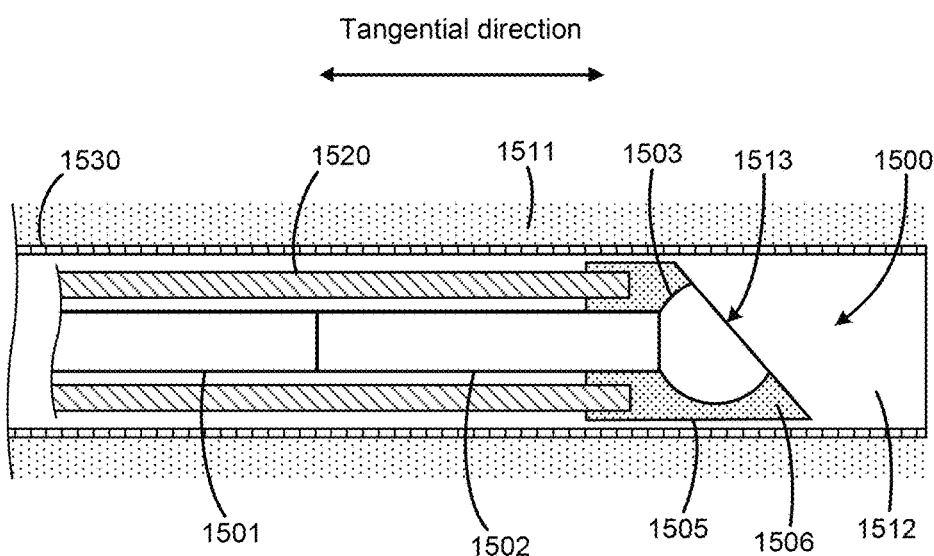
FIG. 15 illustrates a partially-cutaway view of an example embodiment of an optical-imaging device that includes an optical probe, a drive cable, and a sheath.

FIG. 15 illustrates a partially-cutaway view of an example embodiment of an optical-imaging device that includes an optical probe, a drive cable, and a sheath. The drive cable 1520 is attached to the optical probe 1500. The optical probe 1500 is surrounded by an inner medium 1512, which is contained in the sheath 1530, and the sheath 1530 is surrounded by an outer medium 1511. The optical probe 1500 includes a first light-guiding component 1501, a second light-guiding component 1502, a lens 1503, and a correction component 1505. The correction component is filled with epoxy 1506. Both the lens 1503 and the correction component 1505 have been angle polished to create a light-reflecting surface 1513 (e.g., a TIR surface).

Figure 16:
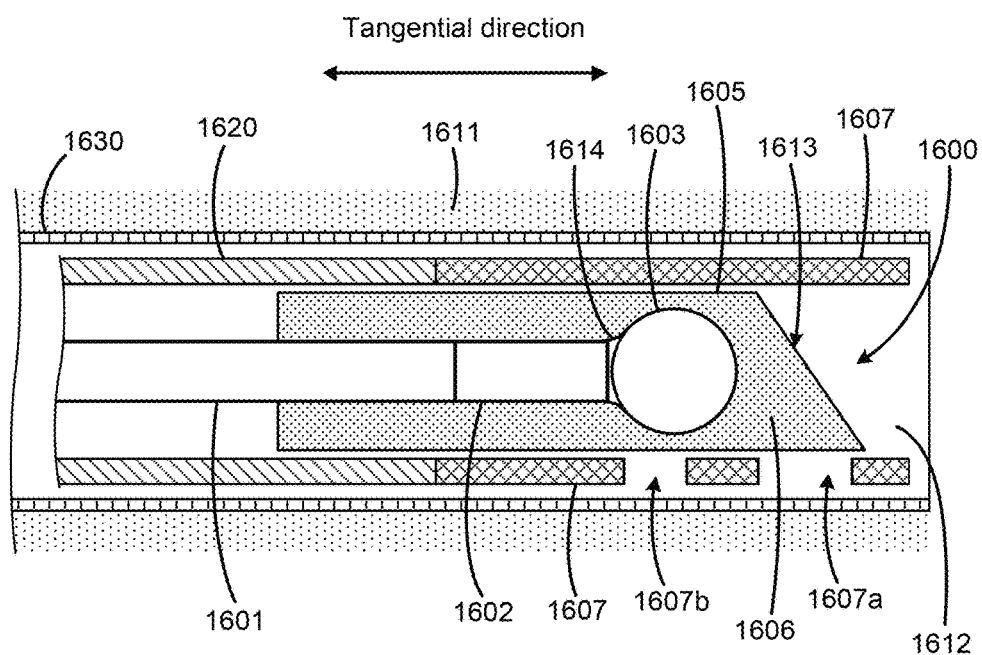
FIG. 16 illustrates a partially-cutaway view of an example embodiment of an optical-imaging device that includes an optical probe, a drive cable, a protector, and a sheath.

FIG. 16 illustrates a partially-cutaway view of an example embodiment of an optical-imaging device that includes an optical probe, a drive cable, and a sheath. The optical probe 1600 is surrounded by an inner medium 1612, which is contained in the sheath 1630, and the sheath 1630 is surrounded by an outer medium 1611. The optical probe 1600 includes a first light-guiding component 1601, a second light-guiding component 1602, a ball lens 1603, and a correction component 1605. In this embodiment, the ball lens 1603 is attached to the second light-guiding component 1602 by epoxy 1614 or another adhesive. Also, the correction component 1605 is a tube (e.g., a glass tube, a sapphire tube, a heat-shrink tube) that is filled with epoxy 1606 or another adhesive. During the assembly of some embodiments, the tube is placed over the ball lens 1603, and then the tube is filled with epoxy 1606.

The correction component 1605 includes a light-reflecting surface 1613. Thus, in this embodiment, the correction component 1605 is also a light-reflecting component.

A protector 1607 may be attached to (e.g., fused to, epoxied to) the drive cable 1620, and, in some embodiments, to the optical probe 1600. Also, this embodiment of a protector 1607 has two holes. The first hole 1607a is positioned to allowed the light that has been reflected by the light-reflecting surface 1613 to exit the protector 1607, and the second hole 1607b is for applying epoxy during assembly of the optical probe 1600, for example to attach the optical probe 1600 to the drive cable 1620, to attach the optical probe 1600 to the protector 1607, or to attach the ball lens 1603 to the second light-guiding component 1602. And in some embodiments, the protector 1607 is made of metal.

Also, a protector 1607 may be added to the other embodiments that are described herein (e.g., in FIGS. 2, 7, 10, 13, 14, and 15). For example, a protector may be added to the embodiment that is described in FIG. 14, and, in such embodiments, the correction component 1405 may have an outer diameter that is small enough to fit inside an inner diameter of the protector.

Figure 17:
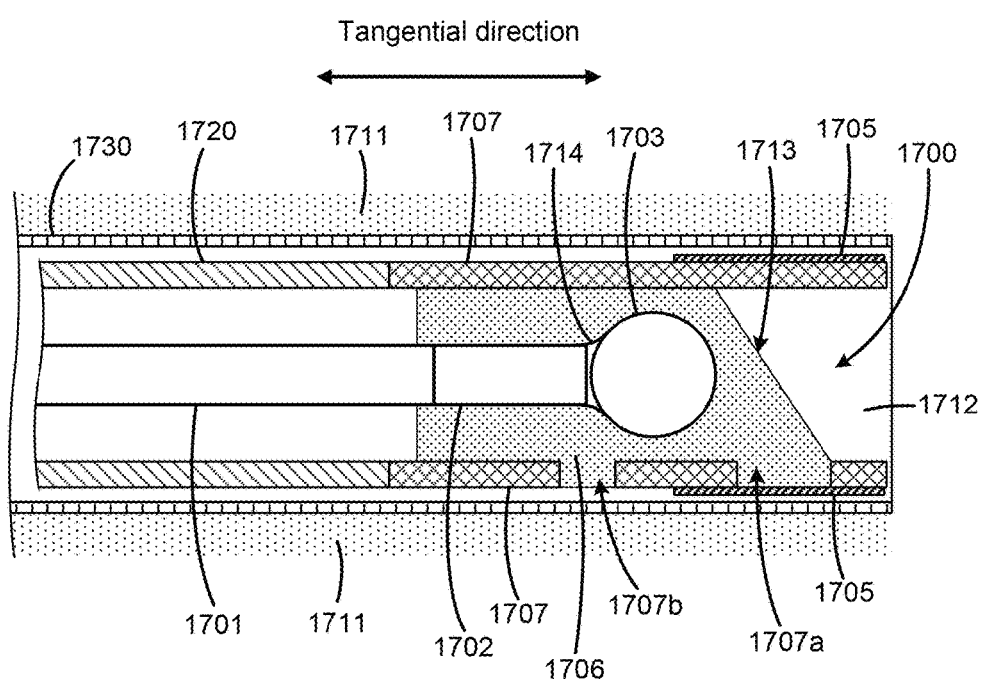
FIG. 17 illustrates a partially-cutaway view of an example embodiment of an optical-imaging device that includes an optical probe, a drive cable, a protector, and a sheath.

FIG. 17 illustrates a partially-cutaway view of an example embodiment of an optical-imaging device that includes an optical probe, a drive cable, a protector, and a sheath. The optical probe 1700 is surrounded by an inner medium 1712, which is contained in the sheath 1730, and the sheath 1730 is surrounded by an outer medium 1711. In some embodiments, the inner medium 1712 is air and the outer medium 1711 is a contrast agent (e.g., n=1.45); consequently, some embodiments of the sheath 1730 have a negative optical power. The optical probe 1700 includes a first light-guiding component 1701, a second light-guiding component 1702, a ball lens 1703, a correction component 1705, epoxy 1706, and a protector 1707. In this embodiment, the ball lens 1703 is attached to the second light-guiding component 1702 by epoxy 1714 or another adhesive. Also, some embodiments of the optical probe 1700 include a different type of lens (e.g., a GRIN lens) than the ball lens 1703. Additionally, in some embodiments, the ball lens 1703 (or GRIN lens) is attached to the second light-guiding component 1702 using fusion-splicing technology.

The protector 1707 may be attached to (e.g., fused to, epoxied to) the drive cable 1720. Also, this embodiment of a protector 1707 has two openings. A distal opening 1707a is positioned to allowed the light that has been reflected by a light-reflecting surface 1713 to exit the protector 1707, and a proximal opening 1707b can be used to apply epoxy during the assembly of the optical probe 1700, for example to attach the optical probe 1700 to the drive cable 1720 or to attach the other members of the optical probe 1700 to the protector 1707.

Also, the correction component 1705 is an optically-transparent tube (e.g., a glass tube, a sapphire tube, a heat-shrink tube) that surrounds at least part of the protector 1707. The epoxy 1706 fills part of the space inside the correction component 1705 and the protector 1707. The epoxy 1706 also forms the light-reflecting surface 1713, which may be a TIR surface, at the interface of the epoxy 1706 and the inner medium 1712. The cylindrical surface of the correction component 1705 forms a correcting surface that operates to correct astigmatism. The correcting surface of the correction component 1705 has a positive optical power in the sagittal direction that compensates for the negative optical power of the sheath 1730.

The radius of the ball lens 1703, the refractive indices, and the length of the second light-guiding component 1702 are configured to control the NA, the aperture size, and the working distance. The refractive indices of the epoxy 1706, the correction component 1705, and the sheath 1730, as well as the inner and outer radii of the correction component 1705 and the sheath 1730, are configured such that the positive optical power of the correction component 1705 is close to the negative optical power of the sheath 1730. In some embodiments, the sagittal optical powers of the correction component 1705 and the sheath 1730 can be described by the following:

$$\phi_{correction\ element} + \phi_{sheath} = 0, \text{ and}$$

$$\phi_{sheath} < 0,$$

where $\phi_{correction\ element}$ is the sagittal optical power of the correction component 1705, and where $\phi_{sheath}$ is the sagittal optical power of the sheath 1730.

Figure 18A:
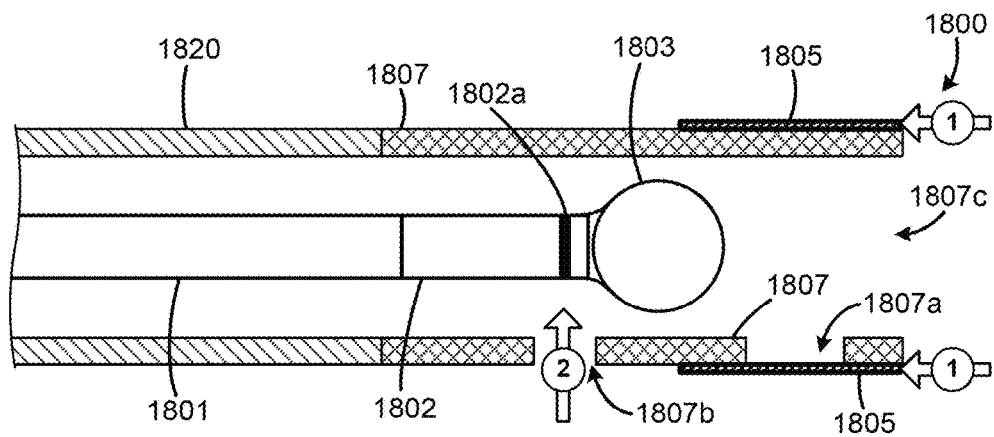
FIGS. 18A-C illustrate an example embodiment of a method for manufacturing an optical probe.
Figure 18B:
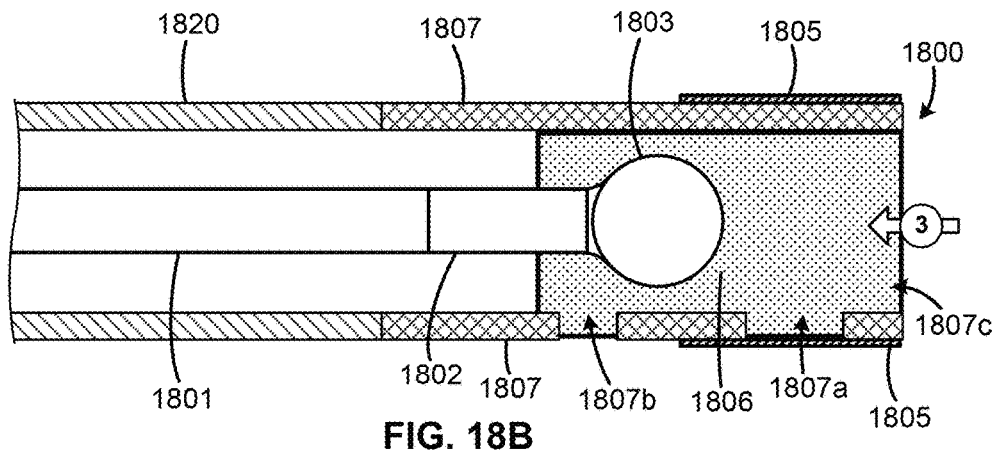
Figure 18C:
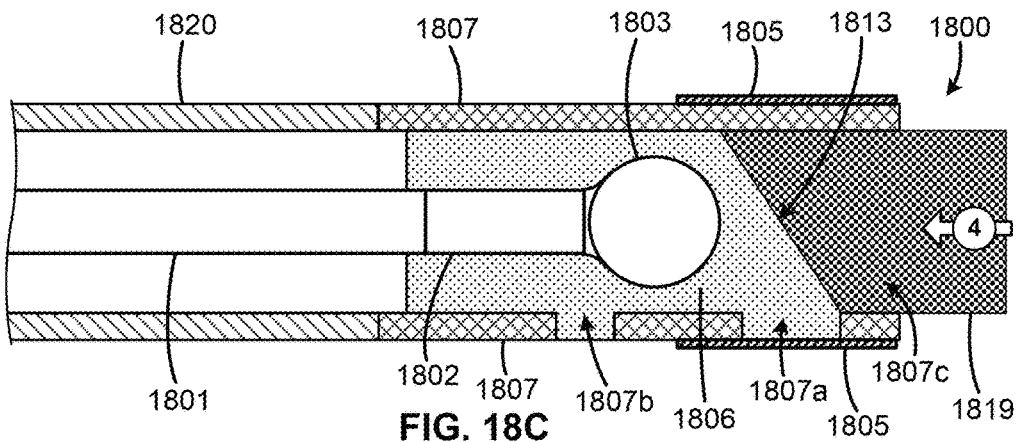

FIGS. 18A-C illustrate an example embodiment of a method for manufacturing an optical probe. Initially, the optical probe 1800 includes a first light-guiding component 1801, a second light-guiding component 1802, a lens 1803, and a protector 1807. The drive cable 1820 is affixed to the protector 1807. In stage 1, a correction component 1805, which is a transparent tube in this example, is placed over the protector 1807. The correction component 1805 covers a distal opening 1807a of the protector 1807.

Next, the lens 1803 is positioned in the correct longitudinal location by observing a position marker 1802a through the proximal opening 1807b of the protector 1807. Once the desired position is reached, then in stage 2 the lens 1803, the first light-guiding component 1801, and the second light-guiding component 1802 are bound to the protector 1807 by injecting epoxy through a proximal opening 1807b.

Next, in stage 3, which is shown in FIG. 18B, more epoxy 1806 is injected into the protector 1807 through an opening in the distal end 1807c of the protector 1807 and an opening in the distal end of the correction component 1805, thereby submerging at least part of the lens 1803 and the distal opening 1807a of the protector 1807 in the epoxy 1806.

Before the epoxy 1806 cures, in stage 4, which is shown in FIG. 18C, an angle-polished mandrel 1819 is inserted through the opening in the distal end 1807c of the protector 1807 and the opening in the distal end of the correction component 1805. This pushes the epoxy 1806 in the proximal direction and forms an angled surface 1813. The mandrel 1819 is positioned such that the angled surface 1813 is aligned to reflect light from the lens 1803 through the distal opening 1807a of the protector 1807.

Finally, in stage 5, the epoxy 1806 is cured, and then in stage 6 the mandrel 1819 is removed. The mandrel 1819 may have a coating such that its surface is smooth and easy to detach from the epoxy 1806. Once the curing is finished, removing the mandrel 1819 leaves the angled surface 1813, which may be a TIR surface. Also, in some embodiments, some curing is done after the mandrel 1819 is removed.

In some embodiments, the mandrel 1819 has a key (or a slot) that indicates the orientation of the angled surface 1813, and the protector 1807 has a complimentary slot (or a key) that indicates the orientation of the distal opening 1807a on the protector 1807. During fabrication, an operator can use the key and slot to align the orientation of the mandrel 1819 to the protector 1807 so that light that is reflected by the angled surface 1813 will exit through the distal opening 1807a.

Figure 19B:
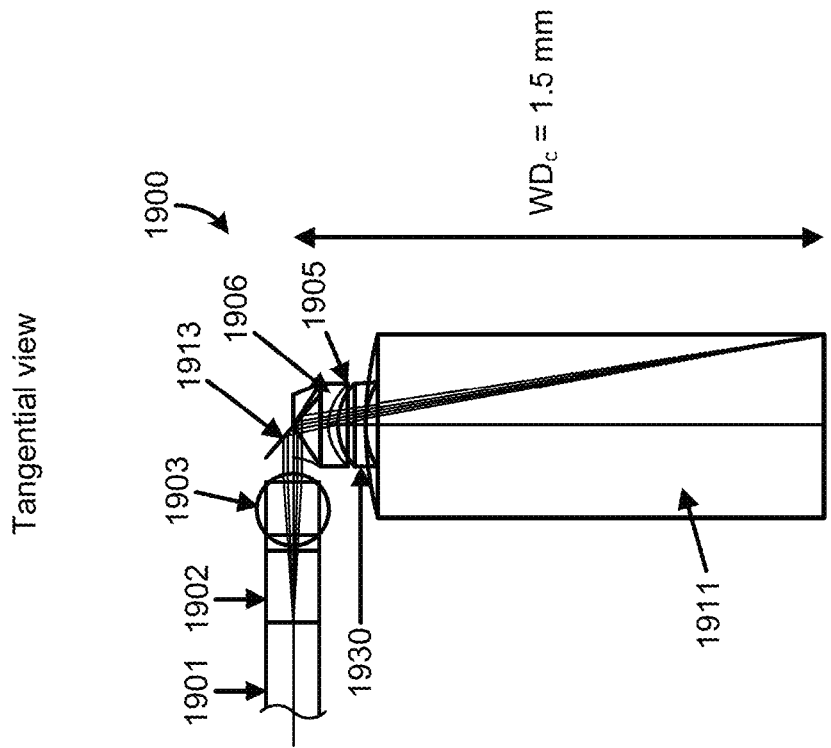
FIGS. 19A-B illustrate a sagittal view and a tangential view of an example embodiment of an optical-imaging device that includes an optical probe and a sheath.
Figure 19A:
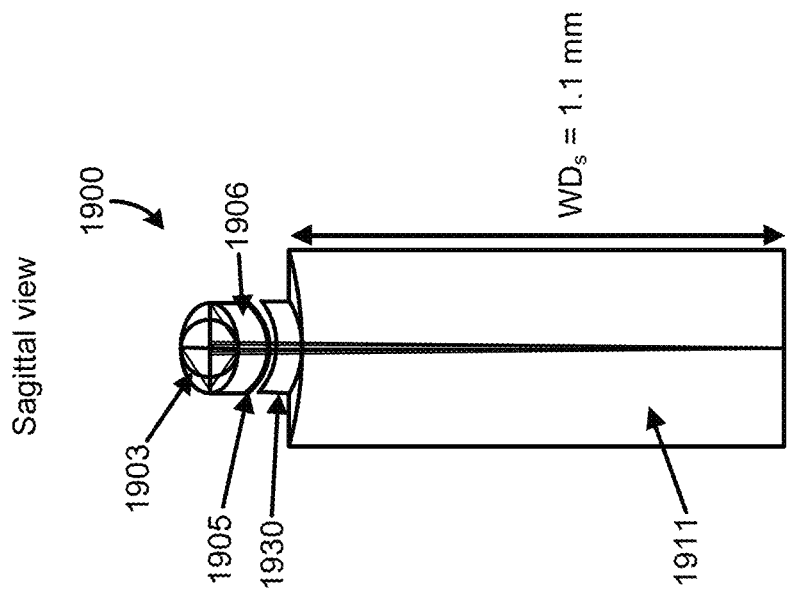

FIGS. 19A-B illustrate a sagittal view and a tangential view of an example embodiment of an optical-imaging device that includes an optical probe and a sheath. FIGS. 19A-B show the transmission of light that has a wavelength λ of 1.31 μm (λ=1.31 μm) by the optical probe 1900 and the sheath 1930.

In this embodiment, the first light-guiding component 1901 is a double-clad fiber with a NA of 0.09. Light that exits the first light-guiding component 1901 then passes through the second light-guiding component 1902, which is a 350 μm length of coreless fiber (e.g., fused silica), and then enters a sapphire ball lens 1903, which has a diameter of 350 μm. Then the light travels through the epoxy 1906 and is reflected by the light-reflecting surface 1913, and then the light passes through a cylindrical surface 1905 that has an optical power only in the sagittal direction. The cylindrical surface is part of the correction component 1905 (e.g., an epoxy-filled PET heat-shrink tube) that covers the protector 1907. The light then exits through the sheath 1930, which has an optical power only in the sagittal direction.

In this embodiment, the epoxy 1906 has refractive index of 1.37 (n=1.37), and the correction component 1905 has an inner diameter of 512 μm, a wall thickness of 6 μm, and a refractive index of approximately 1.65. Also, the light-reflecting surface 1913 is angled such that the chief ray from the lens 1903 has an incident angle of approximately 50° to the normal of the TIR surface 1913. Additionally, the chief ray's incident angle to the sheath 1930 in the tangential direction is about 20° in air.

The air gap between the correction component 1905 and the sheath 1930 is approximately 38 μm. And the sheath 1930 has an inner diameter of approximately 0.6 mm, an outer diameter of 0.8 mm, and a refractive index of approximately 1.5 (n=1.5). The sheath 1930 is immersed inside a contrast agent 1911, which has a refractive index of 1.45 (n=1.45).

The astigmatism of the OCT beam at the wavelength λ of 1.31 μm (λ=1.31 μm) is corrected at a focus point that is 1.5 mm away, measured vertically, from the optical axis of the second light-guiding component 1902, and the focus point is also 1.1 mm away, measured vertically, from the outer diameter of the sheath 1930. Accordingly, the working distance $WD_s$ from the outer diameter of the sheath 1930 is 1.1 mm, and the working distance $WD_c$ from the optical axis of the second light-guiding component 1902 is 1.5 mm.

Figure 20:
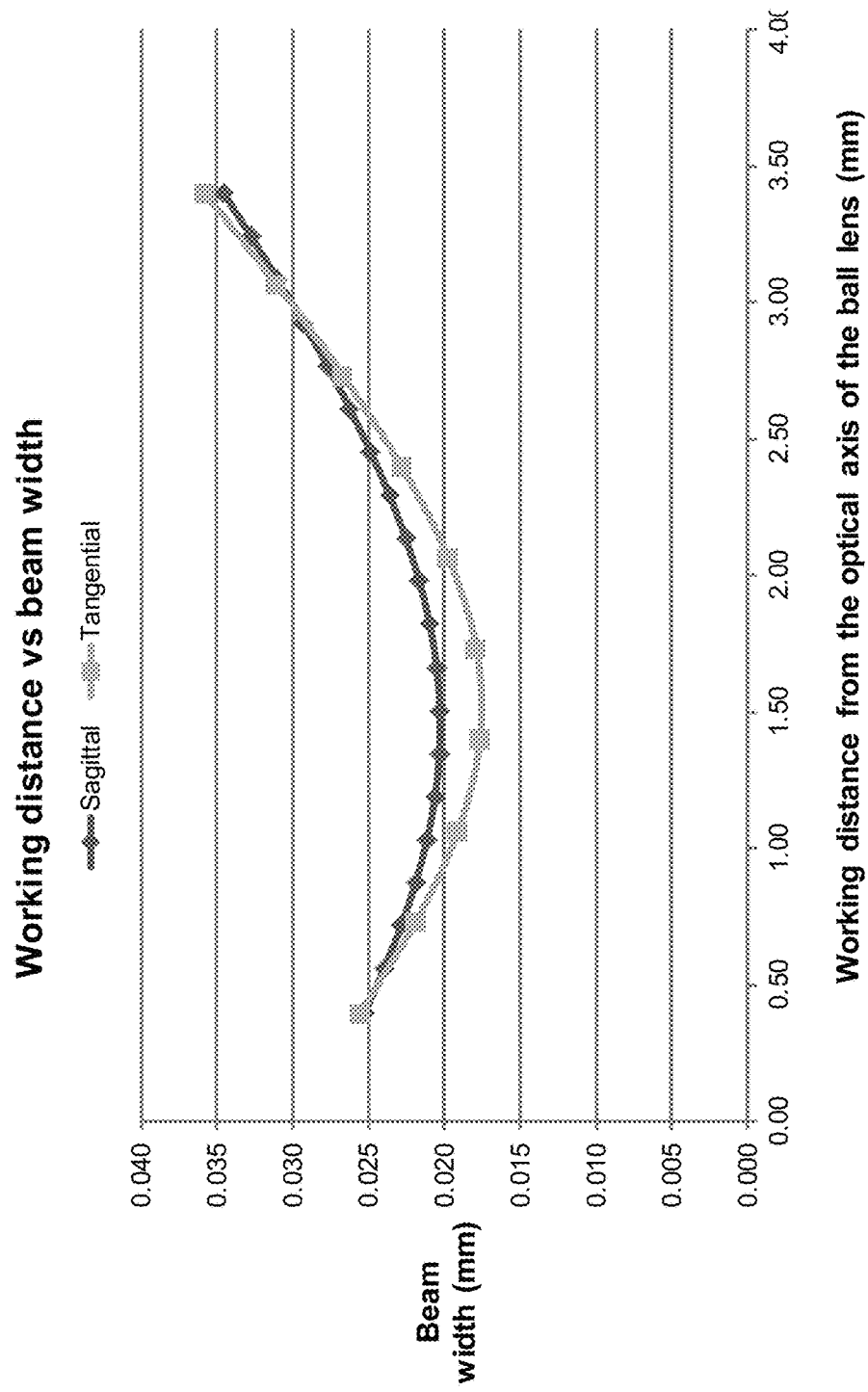
FIG. 20 illustrates the Gaussian beam width of the optical spot radius versus the working distance from the outer diameter of the sheath for the example embodiment of an optical-imaging device that is illustrated in FIGS. 19A-B.

FIG. 20 illustrates the Gaussian beam width of the optical spot radius versus the working distance from the outer diameter of the sheath for the example embodiment of an optical-imaging device that is illustrated in FIGS. 19A-B. FIG. 20 indicates that, in both the tangential and the sagittal directions, the beam of light in the 1.31 μm wavelength focuses at approximately the same distance (at ~1.5 mm from the optical axis of the second light-guiding component 1902).

Figure 21:
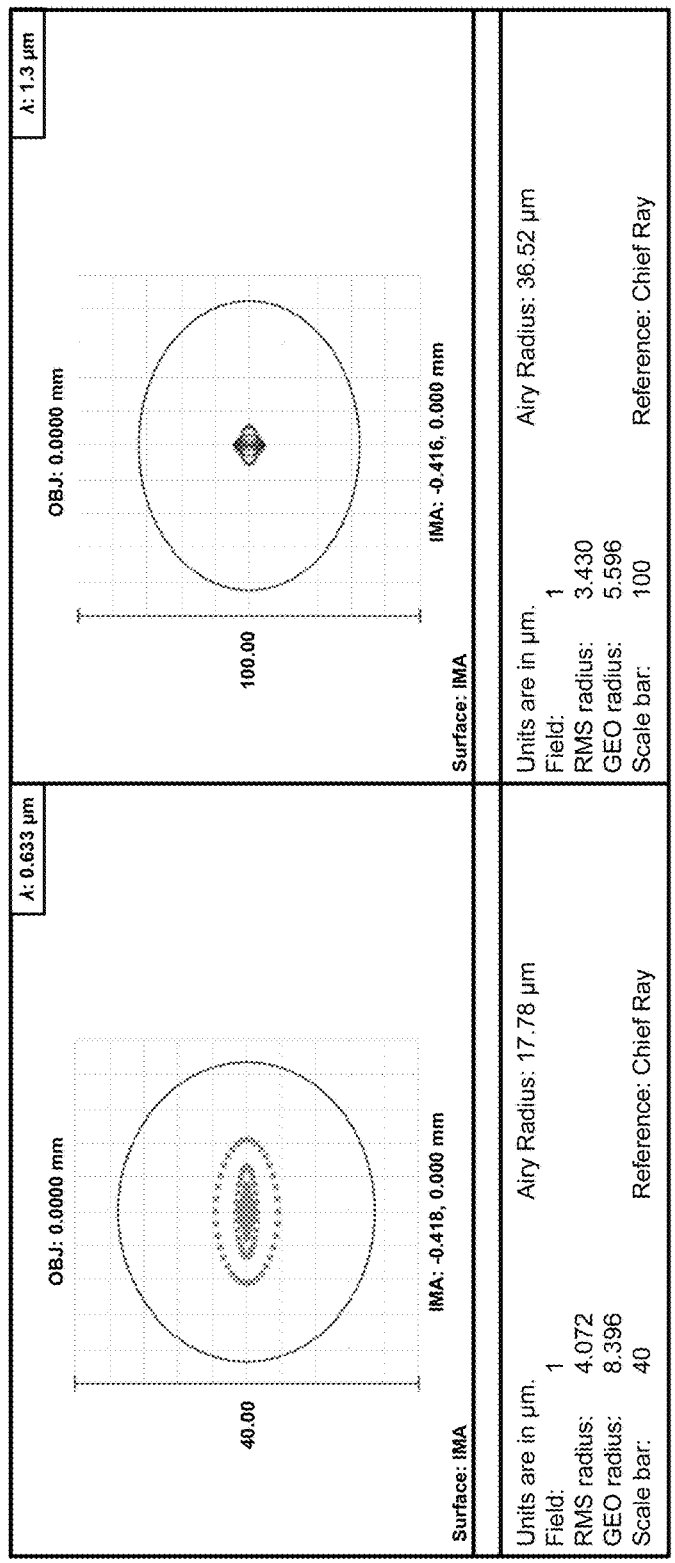
FIG. 21 illustrates the geometrical spot radii in the $\lambda=0.633$ μm and the $\lambda=1.31$ μm wavelengths at a focus point that is 1.5 mm away, measured vertically, from an optical axis of the second light-guiding component in the example embodiment of an optical-imaging device that is illustrated in FIGS. 19A-B.

FIG. 21 illustrates the geometrical spot radii in the λ=0.633 μm and the λ=1.31 μm wavelengths at a focus point that is 1.5 mm away, measured vertically, from an optical axis of the second light-guiding component 1902 in the example embodiment of an optical-imaging device that is illustrated in FIGS. 19A-B. The diffraction limit has a 36.52 μm Airy radius in the wavelength λ of 1.31 μm (λ=1.31 μm) and has a 17.78 μm Airy radius in the wavelength λ of 0.633 μm (λ=0.633 μm).

Figure 22:
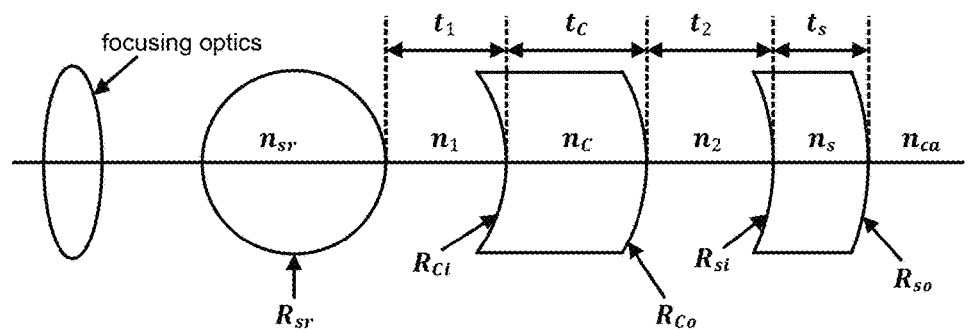
FIG. 22 illustrates an example embodiment of an unfolded optical system in the sagittal plane.

FIG. 22 illustrates an example embodiment of an unfolded optical system in the sagittal plane. In FIG. 22, $n_{sr}$ is the refractive index of a second light-guiding component (e.g., a spacer rod), $n_1$ is the refractive index of the material between the second light-guiding component and the correction component, $n_C$ is the refractive index of the correction component, $n_2$ is the refractive index of the inner medium (e.g., air) between the correction component and the sheath, $n_s$ is the refractive index of the sheath, and $n_{ca}$ the refractive index of the outer medium (e.g., the contrast agent) outside of the sheath. Additionally, $R_{sr}$ is the radius of the second light-guiding component, $R_{Ci}$ is the radius of the inner surface of the correction component, $R_{Co}$ is the radius of the outer surface of the correction component, $R_{si}$ is the radius of the inner surface of the sheath, and $R_{so}$ is the radius of the outer surface of the sheath.

As noted above, the shape of the sheath introduces astigmatism into the optical system. As also noted above, the sagittal optical power of the sheath is negative if $$(n_s - n_2) > \frac{R_{Si}}{R_{So}}(n_s - n_{ca}), \quad (1)$$

where $n_s$ is the refractive index of the sheath, where $n_2$ is the refractive index of the material or materials inside the sheath, and where $n_{ca}$ is the refractive index of the material or materials outside the sheath. Also, $R_{Si}$ is the inner radius of the sheath, and $R_{So}$ is the outer radius of the sheath.

The optical probes that are described herein include an additional optical power such that the optical power in the tangential direction is the same as the sagittal direction:

$$\phi_{tangential} = \phi_{sagittal}. \quad (2)$$

This can be rewritten as follows, where the tangential optical power is written on the left of the equation and the sagittal optical power is expressed on the right:

$$\phi_{fo\_t} + \phi_{sr\_t} = \phi_{fo\_s} + \phi_{sr\_s} + \phi_h + \phi_s, \quad (3)$$

where $\phi_{fo\_t}$ is the optical power of the focusing optics (e.g., a lens) in the tangential direction, where $\phi_{fo\_s}$ is the optical power of the focusing optics in the sagittal direction, where $\phi_{sr\_t}$ is the optical power of the second light-guiding component in the tangential direction, where $\phi_{sr\_s}$ is the optical power of the second light-guiding component in the sagittal direction, where $\phi_h$ is the optical power of the correction component in the sagittal direction, and where $\phi_s$ is the optical power of the sheath in the sagittal direction.

In the embodiments where the focusing optics are rotationally symmetric along the optical axis, the optical powers ($\phi_{fo}$) of the focusing optics in the tangential and sagittal directions are equal. Because $$\phi_{fo\_t} = \phi_{fo\_s},$$

$$\phi_h = \phi_{R_{Ci}} + \phi_{R_{Co}}, \text{ and}$$

$$\phi_s = \phi_{si} + \phi_{so},$$

the following expression is true:

$$\phi_{sr\_s} + \phi_{R_{Ci}} + \phi_{R_{Co}} + \phi_{si} + \phi_{so} = \phi_{sr\_t}. \quad (4)$$

In embodiments where $\phi_{sr\_t} = 0$, equation (4) can be expressed as follows:

$$\frac{n_1 - n_{sr}}{-R_{sr}} + \frac{n_c - n_1}{-R_{Ci}} + \frac{n_2 - n_C}{-R_{Co}} + \frac{n_s - n_2}{-R_{si}} + \frac{n_{ca} - n_s}{-R_{so}} = 0. \quad (5)$$

By properly optimizing the foregoing optical-probe parameters, the negative optical power of the sheath can be balanced and the image quality can be improved.

Figure 23:
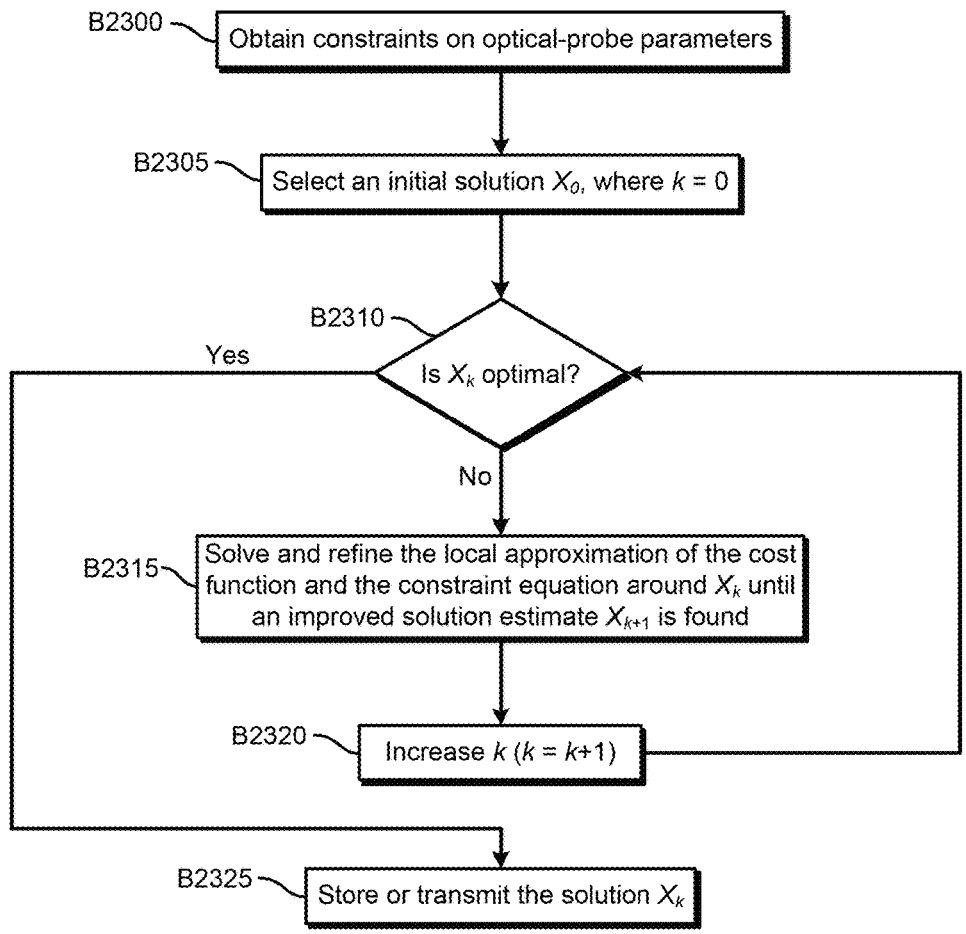
FIG. 23 illustrates an example embodiment of an operational flow for calculating optical-probe parameters.

FIG. 23 illustrates an example embodiment of an operational flow for calculating optical-probe parameters. Although this operational flow is presented in a certain order, some embodiments of this operational flow perform at least some of the operations in different orders than the presented order. Examples of possible different orderings include concurrent, overlapping, reordered, simultaneous, incremental, and interleaved orderings. Thus, other embodiments of the operational flow may omit blocks, add blocks, change the order of the blocks, combine blocks, or divide blocks into more blocks.

Furthermore, although this embodiment of the operational flow is performed by a parameter-optimization device, some embodiments of this operational flow are performed by two or more parameter-optimization devices or by one or more other specially-configured computing devices.

The flow starts in block B2300, where a parameter-optimization device obtains constraints on optical-probe parameters. Using the notation of equation (5), in some embodiments the constraints include the following:

$$R_{Ci} = R_{sr} + t_1,$$

$$R_{Co} = R_{Ci} + t_C,$$

$$R_{si} = R_{Co} + t_2,$$

$$R_{so} = R_{si} + t_s, \text{ and}$$

$$\frac{n_1 - n_{sr}}{-R_{sr}} + \frac{n_c - n_1}{-R_{Ci}} + \frac{n_2 - n_C}{-R_{Co}} + \frac{n_s - n_2}{-R_{si}} + \frac{n_{ca} - n_s}{-R_{so}} = 0.$$

All the constraints may be expressed in a single equation, for example as follows:

$$\frac{n_1 - n_{sr}}{R_{sr}} + \frac{n_c - n_1}{R_{sr} + t_1} + \frac{n_2 - n_C}{R_{sr} + t_1 + t_c} + \frac{n_s - n_2}{R_{sr} + t_1 + t_c + t_2} + \frac{n_{ca} - n_s}{R_{sr} + t_1 + t_c + t_2 + t_s} = 0.$$

Thus, some embodiments of a constraint function F(X) may be expressed as $$F(X) = \frac{n_1 - n_{sr}}{R_{sr}} + \frac{n_c - n_1}{R_{sr} + t_1} + \frac{n_2 - n_C}{R_{sr} + t_1 + t_c} + \frac{n_s - n_2}{R_{sr} + t_1 + t_c + t_2} + \frac{n_{ca} - n_s}{R_{sr} + t_1 + t_c + t_2 + t_s},$$

where $$X = [n_1, n_{sr}, n_c, n_2, n_{ca}, n_s, n_{sr}, t_1, t_2, t_c, t_s].$$

Therefore, the optical-probe parameters can be calculated by solving the optimization problem of minimizing a specific cost function while maintaining the constraint conditions of $$F(X)=0$$

and $$[n_1,n_{sr},n_c,n_2,n_{ca},n_s,R_{sr},t_1,t_2,t_c,t_s]>0.$$

One embodiment of a cost function for this optimization problem is the norm of the gradient J, which can be described as follows:

$$J = \|\nabla F(X)\|^2,$$

where $$\nabla F(X) = \left[\frac{\partial F(X)}{\partial n_1}, \frac{\partial F(X)}{\partial n_{sr}}, \frac{\partial F(X)}{\partial n_c}, \frac{\partial F(X)}{\partial n_{ca}}, \right.$$
$$\left. \frac{\partial F(X)}{\partial n_s}, \frac{\partial F(X)}{\partial n_{sr}}, \frac{\partial F(X)}{\partial t_1}, \frac{\partial F(X)}{\partial t_2}, \frac{\partial F(X)}{\partial t_c}, \frac{\partial F(X)}{\partial t_s}\right]'.$$

Using this cost function to calculate the parameters may make the obtained solution less sensitive to errors in the parameters.

Next, in block B2305, the parameter-optimization device selects an initial solution $X_k$, where k=0. In some embodiments, the initial solution $X_0$ is obtained by fixing some of the parameters based on common knowledge and solving the remaining parameters using trial and error. Then in block B2310, the parameter-optimization device determines if the current solution $X_k$ (which is the initial solution $X_0$ in the first iteration) is optimal. For example, the value of the norm of the gradient J in equation (6) may be an indication of optimality. The smaller the value of the norm of the gradient J, the better the current solution $X_k$ is. If an iteration of blocks B2315-B2320 does not change the value of the norm of the gradient J by much, then the operational flow has reached a local optimal solution, and maybe a global optimal solution. If the current solution $X_k$ is optimal (block B2310=yes), then the flow moves to block B2325, where the parameter-optimization device stores or transmits the current solution $X_k$. If it is not optimal (block B2310=no), then the flow moves to block B2315.

In block B2315, the parameter-optimization device solves and refines the local approximation of the cost function and the constraints around the current solution $X_k$ until an improved solution $X_{k+1}$ is found. This may include solving a nonlinear optimization problem, for example as described by the embodiment of a cost function that is described by equation (6). Then the flow moves to block B2320, where the parameter-optimization device increases k by one (k=k+1), which designates the improved solution $X_{k+1}$ as the current solution $X_k$, and then the flow returns to block B2310.

Figure 24:
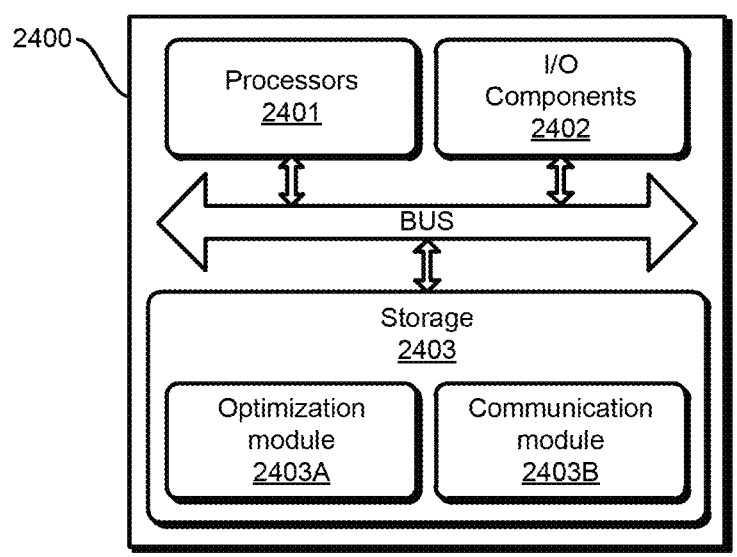
FIG. 24 illustrates an example embodiment of a parameter-optimization device.

FIG. 24 illustrates an example embodiment of a parameter-optimization device. The parameter-optimization device 2400 includes one or more processors 2401, one or more I/O components 2402, and storage 2403. Also, the hardware components of the parameter-optimization device 2400 communicate by means of one or more buses or other electrical connections. Examples of buses include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 2401 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 2402 include communication components (e.g., a GPU, a network-interface controller) that communicate with input and output devices, which may include a keyboard, a display device, a mouse, a printing device, a touch screen, a light pen, an optical-storage device, a scanner, a microphone, a drive, a game controller (e.g., a joystick, a control pad), and a network.

The storage 2403 includes one or more computer-readable storage media. As used herein, a computer-readable storage medium, in contrast to a mere transitory, propagating signal per se, refers to a computer-readable media that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). Also, as used herein, a transitory computer-readable medium refers to a mere transitory, propagating signal per se, and a non-transitory computer-readable medium refers to any computer-readable medium that is not merely a transitory, propagating signal per se. The storage 2403, which may include both ROM and RAM, can store computer-readable data or computer-executable instructions.

The parameter-optimization device 2400 also includes an optimization module 2403A and a communication module 2403B. A module includes logic, computer-readable data, or computer-executable instructions, and may be implemented in software (e.g., Assembly, C, C++, C#, Java, BASIC, Perl, Visual Basic), hardware (e.g., customized circuitry), or a combination of software and hardware. In some embodiments, the parameter-optimization device 2400 includes additional or fewer modules, the modules are combined into fewer modules, or the modules are divided into more modules. When the modules are implemented in software, the software can be stored in the storage 2403.

The optimization module 2403A includes instructions that, when executed, or circuits that, when activated, cause the parameter-optimization device 2400 to calculate optical-probe parameters, for example as described in FIG. 23.

The communication module 2403B includes instructions that, when executed, or circuits that, when activated, cause the parameter-optimization device 2400 to communicate with one or more other computing devices, for example by means of a network.

The scope of the claims is not limited to the above-described embodiments and includes various modifications and equivalent arrangements. Also, as used herein, the conjunction "or" generally refers to an inclusive "or," although "or" may refer to an exclusive "or" if expressly indicated or if the context indicates that the "or" must be an exclusive "or."

The invention claimed is:

1. A device comprising:
   a light-guiding component;
   an optical component;
   a light-reflecting surface that is configured to receive light from the optical component and direct the light along a path; and
   a correction component, wherein the correction component lies in the path, wherein the correction component has an optical power, and wherein the correction component has a center of curvature that substantially coincides with an optical axis of the optical component.

2. The device of claim 1, wherein the optical component includes a gradient-index lens or a ball lens and includes a glass rod or a coreless fiber.

3. The device of claim 1, wherein the light-guiding component is a single-mode optical fiber, a multimode optical fiber, or a double-clad optical fiber.

4. The device of claim 1, wherein the correction component includes the light-reflecting surface.

5. The device of claim 1, wherein the correction component includes a light-exiting surface,
wherein the light-exiting surface has an optical power in a sagittal direction.

6. The device of claim 1, wherein the correction component includes a first light-exiting surface, and
wherein the device of claim 1 further comprises:
a light-reflecting component that includes the light-reflecting surface and includes a second light-exiting surface that acts as another correction component.

7. The device of claim 1, further comprising a sheath that surrounds the light-guiding component, the optical component, the light-reflecting surface, and the correction component,
wherein the sheath has a negative optical power in a sagittal direction.

8. The device of claim 7, wherein the correction component has a net positive optical power in the sagittal direction.

9. The device of claim 8, wherein a net optical power in the sagittal direction of the positive optical power of the correction component and of the negative optical power of the sheath is essentially zero.

10. The device of claim 1, wherein the correction component surrounds at least part of the optical component or at least part of the light-reflecting surface.

11. The device of claim 1, wherein the correction component has a cylindrical shape.

12. The device of claim 1, wherein the correction component is an epoxy-filled tube.

13. The device of claim 1, wherein the correction component is a double-layer tube.

14. The device of claim 1, wherein the correction component corrects an astigmatism in a wavelength of light for optical-coherence-tomography imaging.

15. The device of claim 1, wherein the correction component corrects an astigmatism in a wavelength of light for fluorescence excitation.

16. The device of claim 1, wherein the correction component corrects an astigmatism in a wavelength of light for optical-coherence-tomography imaging,
wherein the correction component corrects an astigmatism in a wavelength of light for fluorescence excitation, and
wherein a mean focal distance of the wavelength of light for optical-coherence-tomography imaging is within 2 mm of a mean focal distance of the wavelength of light for fluorescence excitation.

17. A device comprising:
an optical fiber;
a spacer;
a lens;
a light-reflecting component that is configured to receive light from the lens and direct the light along a path; and
a correction component, wherein the correction component includes a material that is at least partially transparent, wherein the correction component has an optical power in a sagittal direction, and wherein the correction component lies along the path such that the light from the light-reflecting component travels through the material that is at least partially transparent.

18. The device of claim 17, wherein the correction component has a center of curvature that coincides with an optical axis of the lens.

19. The device of claim 17, wherein the correction component encircles the lens.

20. The device of claim 17, wherein the correction component encircles the light-reflecting component.

21. The device of claim 17, wherein the correction component has a cylindrical shape.

22. A device comprising:
a lens;
a light-reflecting component that is configured to receive light from the lens and direct the light along a path; and
a correction component, wherein the correction component has an optical power in a sagittal direction, and wherein the correction component lies along the path such that correction component transmits the light from the light-reflecting component.

23. The device of claim 22, wherein the correction component has a center of curvature that coincides with an optical axis of the lens.

24. The device of claim 23, wherein the lens is a GRIN lens.

25. The device of claim 23, wherein the lens is a ball lens.

26. The device of claim 22, wherein the correction component is part of the light-reflecting component.

27. The device of claim 22, further comprising:
a sheath that has an optical power in the sagittal direction,
wherein a net optical power in the sagittal direction of the optical power of the correction component and the optical power of the sheath is essentially zero.

28. A device comprising:
a light-guiding component;
an optical component;
a light-reflecting surface that is configured to receive light from the lens and direct the light along a path; and
means for producing a positive optical power in a sagittal direction, wherein the means for producing the positive optical power in the sagittal direction lies in the path.

* * * * *